United States Patent

Fodor et al.

Patent Number: 5,601,971
Date of Patent: *Feb. 11, 1997

[54] HARDENING OF HYDROPHILIC COLLOIDS WITH IMIDAZOLIUM AND TRIAZINE COMBINATIONS

[75] Inventors: Ludovic Fodor; Richard R. M. Jones, both of Hendersonville, N.C.; Reinhold Rüger, Rödermark, Germany; Timothy D. Weatherill, Hendersonville; Rolf T. Weberg, Brevard, both of N.C.

[73] Assignee: Sterling Diagnsotic Imaging, Inc., Glasgow, Del.

[ * ] Notice: The term of this patent shall not extend beyond the expiration date of Pat. No. 5,459,029.

[21] Appl. No.: 401,057

[22] Filed: Mar. 8, 1995

Related U.S. Application Data

[63] Continuation-in-part of Ser. No. 208,778, Mar. 11, 1994, abandoned, and Ser. No. 36,380, Mar. 24, 1993, abandoned, which is a continuation of Ser. No. 817,629, Jan. 7, 1992.

[30] Foreign Application Priority Data

Jun. 18, 1991 [DE] Germany .......................... 41 19 982.0

[51] Int. Cl.$^6$ ................................ G03C 1/30; B05D 3/04
[52] U.S. Cl. ................. 430/621; 430/623; 430/626; 430/640; 430/935; 427/338; 530/354; 106/125
[58] Field of Search ..................... 430/623, 621, 430/640, 935, 626; 427/338, 414; 530/354; 106/125

[56] References Cited

U.S. PATENT DOCUMENTS

| | | | |
|---|---|---|---|
| 3,288,775 | 11/1966 | Anderau et al. | 260/117 |
| 3,325,287 | 6/1967 | Yamamoto et al. | 96/111 |
| 3,549,377 | 12/1970 | Meckl et al. | 96/111 |
| 3,880,665 | 4/1975 | Himmelmann | 96/111 |
| 4,063,952 | 12/1977 | Himmelmann et al. | 96/111 |
| 4,181,529 | 1/1980 | Sels et al. | 430/626 |
| 4,187,114 | 2/1980 | Kokelenberg et al. | 430/510 |
| 4,216,108 | 8/1980 | Sels et al. | 252/182 |
| 4,618,570 | 10/1986 | Kadowaki et al. | 430/505 |
| 4,710,456 | 12/1987 | Naoi et al. | 430/564 |
| 4,874,687 | 10/1989 | Itabashi | 430/446 |
| 4,944,966 | 7/1990 | Jerenz | 427/397 |
| 5,034,249 | 7/1991 | Reif et al. | 427/338 |
| 5,391,477 | 2/1995 | Weatherill | 430/642 |
| 5,459,029 | 10/1995 | Fodor et al. | 430/621 |

FOREIGN PATENT DOCUMENTS

0345514A2  12/1989  European Pat. Off. .

Primary Examiner—Thorl Chea
Attorney, Agent, or Firm—Joseph T. Guy, Jr.

[57] ABSTRACT

An improved method of hardening a hydrophilic colloid is detailed. The hardening results in a stronger matrix and less water pickup. These and other advantages are obtained by hardening with a combination of at least one hardener chosen from Formula I either alone or in combination with at least one hardener chosen from Formula II:

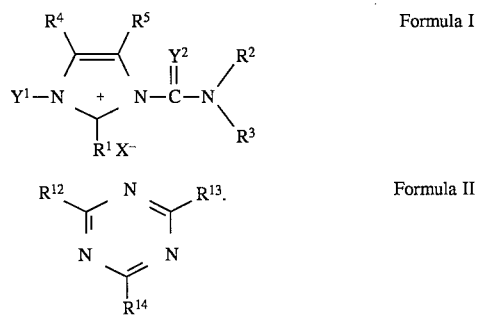

The substituents are defined.

28 Claims, No Drawings

HARDENING OF HYDROPHILIC COLLOIDS WITH IMIDAZOLIUM AND TRIAZINE COMBINATIONS

RELATED APPLICATIONS

This application is a continuation-in-part of Ser. No. 08/208,778 filed Mar. 11, 1994, now abandoned, and a continuation-in-part of Ser. No. 08/036,380 filed Mar. 24, 1993, now abandoned, which is in-turn a continuation of Ser. No. 07/817,629 filed Jan. 7, 1992.

FIELD OF INVENTION

This invention is related to improved hardeners for proteinaceous materials. Specifically this invention is related to new carbamoyl imidazolium compounds and their use in a process for hardening gelatin coatings, particularly coatings of photographic recording materials. More specifically this invention is related to a combination of a carbamoyl imidazolium compound used alone or in combination with triazine hardeners for crosslinking a proteinaceous material in a photographic film.

BACKGROUND OF THE INVENTION

Proteinaceous materials are used for a wide variety of applications. Predominant useful properties are their ability to swell in aqueous solutions and yet form a solid matrix which is permeable to aqueous solutions upon drying. These properties have been exploited for many generations in the field of photographic sciences and proteinaceous materials are still widely used as a binder for harbouring silver halide grains in the photosensitive layer of photographic films. A particular type of proteinaceous material is gelatin as commonly employed in gelatin coatings.

Gelatin coatings are used in various fields of technology, for example, as protective coatings on objects or as binder coatings for reagents in materials for analytical or diagnostic purposes, or for light-sensitive materials, preferably silver halides, in photographic recording materials. For practical use, these coatings are hardened by the addition of a hardener. Known hardeners act by cross-linking the gelatin as a result of a reaction with its free amino, imino, or hydroxyl groups.

Formation of a solid matrix is typically considered to be a result of inter-and intra-molecular hydrogen bonding within both the helical and random regions of proteinaceous materials. If only the natural hydrogen bonding is employed the strength of the matrix is typically insufficient for use in a photographic film. Therefore, it is common practice to add a hardener, also known as a crosslinking agent, to a proteinaceous material when used for photographic layers.

For this purpose, it is desirable that the hardening reaction be complete shortly after layer formation. Thus, the coatings attain their complete functionality, based on hardening, immediately after manufacture. Particularly in photographic recording materials, this avoids, for a long time after manufacture, changes in photographic properties as a result of the so-called "afterhardening".

Hardeners are chosen, in part, for their ability to link one group on a proteinaceous molecule with another group on the same, or different, proteinaceous molecule. The linking generates a three dimensional network of proteinaceous material. This three-dimensional network has sufficient strength to safely harbour a silver halide grain. Another important aspect of the three dimensional network is an ability to allow solution to permeate freely during the photographic processing steps of development, fixing (or bleaching) and washing. It is imperative that the solution which freely permeates the matrix is not strongly absorbed. This is particularly important for photosensitive elements since they must often be capable of transiting the photographic processing steps of development, fixing, washing and drying in 20–120 seconds.

Crosslinking of a binder matrix most often involves the carboxyl groups, amine groups, or combinations thereof. The number of carboxyl groups is substantially larger than the number of amine groups in most commercially available gelatin. Traditional hardeners, such as triazines, are widely accepted as capable of combining amine groups and are thus termed amine-amine crosslinkers. Amine-amine crosslinkers provide a very strong matrix yet the carboxyls are largely unaffected. The unreacted carboxyl groups are deleterious since they strongly absorb processing solutions and increase the time required to remove the absorbed solution. The result is an increase in the time and/or energy required for transiting the photographic processing steps identified above. Peptide couplers, such as imidazoliums, are widely accepted as combining a carboxyl group with an amine group to form an amide linkage between binder strands. This is advantageous since the number of free carboxyls is decreased. Unfortunantly, the strength of the peptide-coupled binder is insufficient to transit a processor and total binder destruction is frequently observed.

Peptide couplers generally react very quickly relative to amine-amine crosslinkers. Therefore, the availability of free amine groups is expected to be diminished after peptide coupling. The diminished number of available amine groups is expected to decrease the effectiveness of amine-amine crosslinking and therefore the two methods of crosslinking are considered in the art to be competitive as opposed to complementary.

There has been a long felt need in the art to provide a method of crosslinking a binder which has the strength of an amine-amine crosslinked matrix and the permeability and low solution retention of a binder crosslinked by amide linkages.

So-called instant hardeners are described, for example, in Reif, U.S. Pat. No. 5,034,249; Liebe, German Patent 3,819, 082 (European Patent Application 345,514); Himmelmann, U.S. Pat. No. 4,063,952 (German Patent 2,439,551); and Himmelmann, U.S. Pat. No. 3,880,665 (German Patents 2,317,677 and 2,225,230). In these hardeners, a carbamoyl group doubly substituted on the nitrogen is linked to a quaternized nitrogen atom of a heterocyclic ring, generally a pyridine ring. Imidazolium rings are not disclosed and the rings described in the prior art are inferior to imidazolium for the reasons set forth herein.

However, the known instant hardeners are only slightly stable in aqueous solution. It is therefore not possible to prepare a supply of aqueous solutions of these compounds for practical use, because the hardening effect decreases with time as the content of the reactive material decreases in storage. In addition, solutions and coatings prepared with pyridinium hardeners have an unpleasant pyridine odor in use.

An important consideration in crosslinking a binder is the pH of activity. This is particularly important when comparing amine-amine crosslinking reactions with reactions that form amide linkages. Amine-amine crosslinkers, like triazines, are typically stable around a neutral pH (~7) and decomposition, or decreased reactivity, is observed above or below neutrality. Peptide couplers, especially imidazoliums, are susceptible to instablility at higher pH and decomposition is accelerated above a pH of approximately 6.2. Therefore, if a pH is employed for optimum amine-amine crosslinking, the decomposition of imidazolium complexes is in competition with crosslinking reactivity. If a pH is employed which is suitable for formation of amide linkages by an imidazolium, the amine-amine crosslinking reagents become unstable in solution. At intermediate ranges neither crosslinking method is efficient. Partly due to the stability differences, skilled artisans have considered imidazolium type coupling agents and amine-amine coupling agents to be incompatable since a suitable solution pH was unavailable. By methods described herein the advantages of imidazolium couplers and amine-amine couplers can be used concurrently to provide a strong matrix with low water absorption.

Therefore, the problem involved in the invention is to provide instant hardeners that are stable in aqueous solution and yield odor-free, hardened coatings in practice.

SUMMARY OF THE INVENTION

It is an object of the present invention to provide a novel composition for hardening hydrophilic colloids which effectively increases the strength of the matrix.

It is another object of the present invention to provide a novel composition for hardening hydrophilic colloids which decreases the amount of fluid absorbed and restrained during processing.

It is yet another object of the present invention to provide a combination of hardeners which are suitable for use in a photographic element.

A particular feature of the present invention is the ability to provide a photographic element which has a strong matrix, low fluid absorption and can undergo photographic development without detrimental effects.

Other advantages, as will be apparant from the description herein, are provided in a photographic element comprising a photosensitive layer and a first hydrophilic colloid layer hardened with 0.01 to 1.0 millimoles per gram of hydrophilic colloid of at least one imidazolium compound of formula:

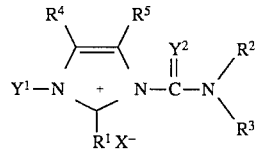

wherein:

$Y^1$ is an alkyl of 1 to 24 carbons; aryl of 6 to 24 carbons; aralkyl of 7 to 25 carbons; a 5- or 6-membered ring containing atoms chosen from a set consisting of C, N, O, and S; $—L^1CR^8CH_2$ or a polymer thereof; $—C(Y^4)E$; or

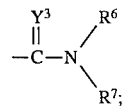

E is an alkyl of 1 to 24 carbons; aryl of 6 to 24 carbons; aralkyl of 7 to 25 carbons; $—OR^9$; $—CN$; or a 5- or 6-membered ring containing atoms chosen from a set consisting of C, N, O, and S;

$L^1$ is a linking group;

$R^1$ is hydrogen; alkyl of 1 to 24 carbons; aryl of 6 to 24 carbons; aralkyl of 7 to 25 carbons; $—OR^{10}$; halogen; nitro; carboxyl; mercapto; alkylamino of 1 to 24 carbons; or a 5- or 6-membered ring containing atoms chosen from a set consisting of C, N, O, and S;

$R^2$ and $R^3$ independently represent hydrogen; alkyl of 1 to 24 carbons; aryl of 6 to 24 carbons; or aralkyl of 7 to 25 carbons; or $R^2$ and $R^3$ independently represent, or are taken together to represent, a 5- or 6-membered ring containing atoms chosen from a set consisting of C, N, O, and S;

$R^4$ and $R^5$ independently represent hydrogen; alkyl of 1 to 24 carbons; aryl of 6 to 24 carbons; aralkyl of 7 to 25 carbons; nitro; carboxyl; mercapto; $—OR^{11}$; halogen; alkylamino of 1 to 24 carbons; or a 5- or 6-membered ring containing atoms chosen from a set consisting of C, N, O, and S; or $R^4$ and $R^5$ taken together represent a 5- or 6-membered ring containing atoms chosen from a set consisting of C, N, O, and S;

$X^-$ is a counterion;

$Y^2$, $Y^3$ and $Y^4$ independently represent O or S;

$R^6$ and $R^7$ independently represent hydrogen; alkyl of 1 to 24 carbons; aryl of 6 to 24 carbons; aralkyl of 7 to 25 carbons; or a 5- or 6-membered ring containing atoms chosen from a set consisting of C, N, O, and S; or $R^6$ and $R^7$ taken together represent a 5- or 6-membered ring containing atoms chosen from a set consisting of C, N, O, and S;

$R^8$ represents a hydrogen; alkyl of 1 to 24 carbons; $—C(O)R^{28}$; $—CN$; or aryl of 6 to 24 carbons;

$R^9$ represents hydrogen; alkyl of 1 to 24 carbons; or aryl of 6 to 24 carbons;

$R^{10}$ and $R^{11}$ independently represent hydrogen or alkyl of 1 to 5 carbons; and $R^{28}$ represents hydrogen; alkyl of 1 to 24 carbons; alkoxy of 1 to 24 carbons; amine; or alkylamine of 1 to 24 carbons.

Even further advantages are provided in a preferred embodiment as realized in a photographic element comprising a first hydrophilic colloid layer hardened with at least one compound chosen from:

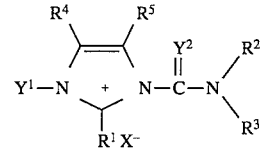

wherein:

$Y^1$ is an alkyl of 1 to 24 carbons; aryl of 6 to 24 carbons; aralkyl of 7 to 25 carbons; a 5- or 6-membered ring containing atoms chosen from a set consisting of C, N, O, and S;

$—L^1CR^8CH_2$, or a polymer thereof; $—C(Y^4)E$; or

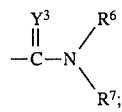

E is an alkyl of 1 to 24 carbons; aryl of 6 to 24 carbons; aralkyl of 7 to 25 carbons; $—OR^9$; $—CN$; or a 5- or 6-membered ring containing atoms chosen from a set consisting of C, N, O, and S;

$L^1$ is a linking group;

$R^1$ is hydrogen; alkyl of 1 to 24 carbons; aryl of 6 to 24 carbons; aralkyl of 7 to 25 carbons; —$OR^{10}$; halogen; nitro; carboxyl; mercapto; alkylamino of 1 to 24 carbons; or a 5- or 6-membered ring containing atoms chosen from a set consisting of C, N, O, and S;

$R^2$ and $R^3$ independently represent hydrogen; alkyl of 1 to 24 carbons; aryl of 6 to 24 carbons; or aralkyl of 7 to 25 carbons; or $R^2$ and $R^3$ independently represent, or are taken together to represent, a 5- or 6-membered ring containing atoms chosen from a set consisting of C, N, O, and S;

$R^4$ and $R^5$ independently represent hydrogen; alkyl of 1 to 24 carbons; aryl of 6 to 24 carbons; aralkyl of 7 to 25 carbons; nitro; carboxyl; mercapto; —$OR^{11}$; halogen; alkylamino of 1 to 24 carbons; or a or 6-membered ring containing atoms chosen from a set consisting of C, N, O, and S; or $R^4$ and $R^5$ taken together represent a 5- or 6-membered ring containing atoms chosen from a set consisting of C, N, O, and S;

$X^-$ is a counterion;

$Y^2$, $Y^3$ and $Y^4$ independently represent O or S;

$R^6$ and $R^7$ independently represent hydrogen; alkyl of 1 to 24 carbons; aryl of 6 to 24 carbons; aralkyl of 7 to 25 carbons; or a 5- or 6-membered ring containing atoms chosen from a set consisting of C, N, O, and S; or $R^6$ and $R^7$ taken together represent a 5- or 6-membered ring containing atoms chosen from a set consisting of C, N, O, and S;

$R^8$ represents a hydrogen; alkyl of 1 to 24 carbons; —$C(O)R^{28}$; —CN; or aryl of 6 to 24 carbons;

$R^9$ represents hydrogen; alkyl of 1 to 24 carbons; or aryl of 6 to 24 carbons;

$R^{10}$ and $R^{11}$ independently represent hydrogen; or an alkyl of 1 to 5 carbons; and $R^{28}$ represents hydrogen; alkyl of 1 to 24 carbons; alkoxy of 1 to 24 carbons; amine; or alkylamine of 1 to 24 carbons; and the first hydrophilic colloid layer or a second hydrophilic colloid layer hardened by at least one triazine compound defined by:

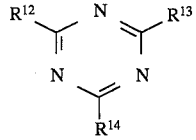

wherein:

at least two of $R^{12}$, $R^{13}$ and $R^{14}$ are independently chosen from a group represented by halogen, preferably Cl or Br;

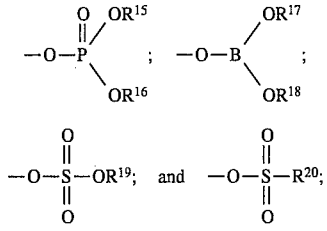

one of $R^{12}$, $R^{13}$ and $R^{14}$ represents hydrogen; alkyl of 1 to 24 carbons; halogen; —$OR^{21}$; —$NR^{22}R^{23}$; —OM; a divalent linking group to another triazine compound; sulfonamide; alkylether of 1 to 20 carbons; polyethylene oxide of 2 to 40 carbons; —$(OR^{24})_xR^{25}$; or —$L^2CR^{26}CH_2$ or a polymer thereof;

$R^{15}$ and $R^{16}$ independently represent sodium; potassium; ammonium; alkyl ammonium of 1 to 20 carbons; hydrogen; or alkyl of 1 to 20 carbons;

$R^{17}$ and $R^{18}$ independently represent sodium; potassium; ammonium; hydrogen; alkyl ammonium of 1 to 20 carbons; or alkyl of 1 to 20 carbons;

$R^{19}$ and $R^{20}$ independently represent sodium; potassium; hydrogen; ammonium; alkyl ammonium of 1 to 20 carbons; or alkyl of 1 to 20 carbons;

$R^{21}$ represents hydrogen; alkyl of 1 to 20 carbons; alkoxyalkyl of 1 to 40 carbons; aryl of 6 to 40 carbons; aralkyl of 7 to 41 carbons; or alkylthioether of 1 to 40 carbons;

$R^{22}$ and $R^{23}$ independently represent hydrogen; alkyl of 1 to 20 carbons; aryl of 6 to 20 carbons; alkylether of 1 to 20 carbons; arylether of 6 to 20 carbons; alkylthioether of 1 to 20 carbons; arylthioether of 6 to 20 carbons; sulfonyl; or alkylsulfonyl of 1 to 20 carbons;

$R^{24}$ represents an ethylene;

$R^{25}$ represents an alkyl of 1 to 20 carbons; or an ether of 1 to 20 carbons;

$R^{26}$ represents a hydrogen; or alkyl of 1 to 24 carbons;

$L^2$ is a chemical linkage;

M is a counterion chosen from sodium, potassium, lithium, calcium, barium, strontium, ammonium, and alkyl ammonium with 1 to 20 carbons; and x is an integer from 1 to 24.

Other advantages are provided in a preferred embodiment of the present invention as observed in a process for forming a photographic element comprising the steps of:

forming at least one liquid photographic emulsion in at least one storage vessel wherein said liquid photographic emulsion comprises silver halide, hydrophilic colloid and a solvent;

transporting said liquid photographic emulsion to an injection region;

injecting into said liquid photographic emulsion in said injection region at least one imidazolium compound defined by

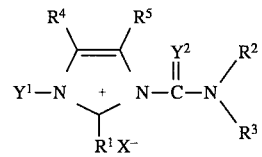

wherein:

$Y^1$ is an alkyl of 1 to 24 carbons; aryl of 6 to 24 carbons; aralkyl of 7 to 25 carbons; a 5- or 6-membered ring containing atoms chosen from a set consisting of C, N, O, and S;

—$L^1CR^8CH_2$ or a polymer thereof; —$C(Y^4)E$; or

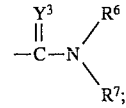

E is an alkyl of 1 to 24 carbons; aryl of 6 to 24 carbons; aralkyl of 7 to 25 carbons; —$OR^9$; —CN; or a 5- or 6-membered ring containing atoms chosen from a set consisting of C, N, O, and S;

$L^1$ is a linking group;

R¹ is hydrogen; alkyl of 1 to 24 carbons; aryl of 6 to 24 carbons; aralkyl of 7 to 25 carbons; —OR¹⁰; halogen; nitro; carboxyl; mercapto; alkylamino of 1 to 24 carbons; or a 5- or 6-membered ring containing atoms chosen from a set consisting of C, N, O, and S;

R² and R³ independently represent hydrogen; alkyl of 1 to 24 carbons; aryl of 6 to 24 carbons; or aralkyl of 7 to 25 carbons; or R² and R³ independently represent, or are taken together to represent, a 5- or 6-membered ring containing atoms chosen from a set consisting of C, N, O, and S;

R⁴ and R⁵ independently represent hydrogen; alkyl of 1 to 24 carbons; aryl of 6 to 24 carbons; aralkyl of 7 to 25 carbons; nitro; carboxyl; mercapto; —OR¹¹; halogen; alkylamino of 1 to 24 carbons; or a 5- or 6-membered ring containing atoms chosen from a set consisting of C, N, O, and S; or R⁴ and R⁵ taken together represent a 5- or 6-membered ring containing atoms chosen from a set consisting of C, N, O, and S;

X⁻ is a counterion;

Y², Y³ and Y⁴ independently represent O or S;

R⁶ and R⁷ independently represent hydrogen; alkyl of 1 to 24 carbons; aryl of 6 to 24 carbons; aralkyl of 7 to 25 carbons; or a 5- or 6-membered ring containing atoms chosen from a set consisting of C, N, O, and S; or R⁶ and R⁷ taken together represent a 5- or 6-membered ring containing atoms chosen from a set consisting of C, N, O, and S;

R⁸ represents a hydrogen; an alkyl of 1 to 24 carbons; —C(O)R²⁸; —CN; or aryl of 6 to 24 carbons;

R⁹ represents hydrogen; alkyl of 1 to 24 carbons; or aryl of 6 to 24 carbons;

R¹⁰ and R¹¹ independently represent hydrogen, or an alkyl of 1 to 5 carbons;

R²⁸ represents hydrogen; alkyl of 1 to 24 carbons; alkoxy of 1 to 24 carbons; amine; or alkylamine of 1 to 24 carbons;

transporting said liquid photographic emulsion to a coater;
coating said liquid photographic emulsion on a substrate; and
removing said solvent from said liquid photographic emulsion.

DETAILED DESCRIPTION OF THE INVENTION

Photographic elements of the present invention comprise one or more binder layers and at least one of the binder layers is crosslinked with at least one compound defined by Formula I, and preferably at least one of the binder layers is crosslinked with a triazine compound defined by Formula II.

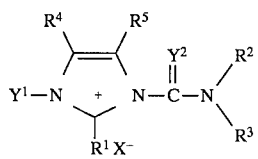

Formula I

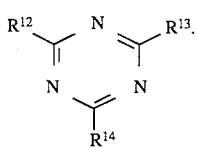

Formula II

Referring specifically to Formula I, Y¹ is an alkyl, or substituted alkyl, of 1 to 24 carbons; aryl, or substituted aryl, of 6 to 24 carbons; aralkyl, or substituted aralkyl, of 7 to 25 carbons; a 5- or 6-membered ring containing atoms chosen from a set consisting of C, N, O, and S; —L¹CR⁸CH₂ or a polymer thereof; —C(Y⁴)E; or

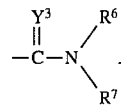

E is an alkyl, or substituted alkyl, of 1 to 24 carbons; aryl, or substituted aryl, of 6 to 24 carbons; aralkyl, or substituted aralkyl, of 7 to 25 carbons; —OR⁹; —CN; or a 5- or 6-membered ring containing atoms chosen from a set consisting of C, N, O, and S. L¹ is a linking group preferably chosen from a covalent chemical bond; alkyl, or substituted alkyl, of 1 to 20 carbons; aryl, or substituted aryl, of 6–24 carbons; aralkyl, or substituted aralkyl, of 7 to 25 carbons; and carboxyl. Most preferably L¹ represents a chemical linkage; or an alkyl, or substituted alkyl, of 1 to 3 carbons. R¹ is hydrogen; alkyl, or substituted alkyl, of 1 to 24 carbons; aryl, or substituted aryl, of 6 to 24 carbons; aralkyl, or substituted aralkyl, of 7 to 25 carbons; halogen; —OR¹⁰; halogen; nitro; carboxyl; mercapto; alklyamino, or substituted alkylamino, of 1 to 24 carbons; or a 5- or 6-membered ring containing atoms chosen front a set consisting of C, N, O, and S. Preferably R¹ represents hydrogen; alkyl, or substituted alkyl, of 1 to 3 carbons; aryl, or substituted aryl, of 6 to 10 carbons; or aralkyl, or substituted aralkyl, of 7 to 11 carbons. Most preferably R¹ represents hydrogen; or alkyl, or substituted alkyl, of 1 to 3 carbons. R² and R³ independently represent hydrogen; alkyl, or substituted alkyl, of 1 to 24 carbons; aryl, or substituted aryl, of 6 to 24 carbons; or aralkyl, or substituted aralkyl, of 7 to 25 carbons. R² and R³ independently can represent, or be taken together to represent, a 5- or 6-membered ring containing atoms chosen from a set consisting of C, N, O, and S. Preferably R² and R³ independently represent alkyl, or substituted alkyl, of 1 to 6 carbons; aryl, or substituted aryl, of 6 to 10 carbons; or aralkyl, or substituted aralkyl, of 7 to 11 carbons; or taken together R² and R³ represent a 5- or 6-membered ring containing atoms chosen from a set consisting of C, N, and O. Most preferably R² and R³ independently represent alkyl, or substituted alkyl, of 1 to 3 carbons or R² and R³ are taken together to represent a 5- or 6-membered ring containing atoms chosen from a set consisting of C, N, and O. If R² and R³ are taken together to represent a 5- or 6-membered ring they can form a 5- or 6-membered saturated ring having 0 or 1 additional nitrogen atoms and 0 or 1 oxygen atoms, and the additional nitrogen atom is unsubstituted or substituted with a methyl, ethyl, or propyl group. R⁴ and R⁵ independently represent hydrogen; alkyl, or substituted alkyl, of 1 to 24 carbons; aryl, or substituted aryl, of 6 to 24 carbons; aralkyl, or substituted aralkyl, of 7 to 25 carbons; nitro; carboxyl; mercapto; —OR¹¹; halogen; or alkylamino, or substituted alkylamino, of 1 to 24 carbons. R⁴ and R⁵ independently can represent a 5- or 6-membered ring containing atoms chosen from a set consisting of C, N, O, and S or R⁴ and R⁵ can be taken together to represent a 5- or 6-membered ring containing atoms chosen from a set consisting of C, N, O, and S. Preferably R⁴ and R⁵ independently represent hydrogen; or alkyl, or unsubstituted alkyl, of 1 to 4 carbon atoms. X⁻ is a counterion. X⁻ can be a halide (e.g., chloride), a complex inorganic ion (e.g., perchlorate), a common organic ion (e.g., tetrafluoroborate), or an anion of a strong acid (e.g., toluene sulfonate). Preferably X⁻ is chosen from a set consisting of halide, CF₃SO₃—, ClO₄—, BF₄— and p—CH₃C₆H₄SO₃—. Y², Y³ and $Y^4$ independently represent O or S. $R^6$ and $R^7$ independently represent hydrogen; alkyl, or substituted alkyl, of 1 to 24 carbons; aryl, or substituted aryl, of 6 to 24 carbons; or aralkyl, or substituted aralkyl, of 7 to 25 carbons. $R^6$ and $R^7$ independently can represent, or be taken together to represent, a 5- or 6-membered ring containing atoms chosen from a set consisting of C, N, O, and S. Preferably $R^6$ and $R^7$ independently represent alkyl, or substituted alkyl, of 1 to 6 carbons; aryl, or substituted aryl, of 6 to 10 carbons; aralkyl, or substituted aralkyl, of 7 to 11 carbons; or taken together $R^6$ and $R^7$ can represent a 5- or 6-membered ring containing atoms chosen from a set consisting of C, N, and O. Most preferably $R^6$ and $R^7$ represent alkyl, or substituted alkyl, of 1 to 3 carbons; or $R^6$ and $R^7$ are taken together to represent a 5- or 6-membered ring containing atoms chosen from a set consisting of C, N, and O. If $R^6$ and $R^7$ are taken together to represent a 5- or 6-membered ring they can form a 5- or 6-membered saturated ring having 0 or 1 additional nitrogen atoms and 0 or 1 oxygen atoms, and the additional nitrogen atom is unsubstituted or substituted with a methyl, ethyl, or propyl group. $R^8$ represents a hydrogen; an alkyl, or substituted alkyl, of 1 to 24 carbons; —C(O)$R^{28}$; —CN; or aryl, or substituted aryl, of 6 to 24 carbons. $R^9$ represents hydrogen; alkyl, or substituted alkyl, of 1 to 24 carbons; or aryl, or substituted aryl, of 6 to 24 carbons. $R^{10}$ and $R^{11}$ independently represent hydrogen; or an alkyl, or substituted alkyl, of 1 to 5 carbons. $R^{28}$ represents hydrogen; alkyl, or substituted alkyl, of 1 to 24 carbons; alkoxy, or substituted alkoxy, of 1 to 24 carbons; amine; or alkyl amine, or substituted alkyl amine, of 1 to 24 carbons.

Consistent with terminology used in the art, the compound represented by:

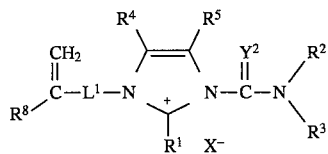

represents a vinyl imidazolium. The vinyl imidazolium has a vinyl group that can be polymerized as known in the art to form a polymer. Preferably the vinyl group of the vinyl imidazolium can be polymerized with other substituted vinyl compounds to form a copolymer. Preferably the vinyl imidazolium is a copolymer defined by:

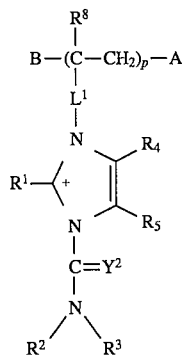

where $R^1$, $R^2$, $R^3$, $R^4$, $R^5$, $R^8$, $L^1$ and $Y^2$ correspond to the definitions above for similiarly referenced groups. The subscript "p" represents the mole fraction of vinyl imidazolium monomer in the polymer and is preferably no more than 95% and more preferably no more than 50%. A and B independently represent copolymerized monomers. Preferably the monomers A and B are independently chosen from a set consisting of acrylic acid ester, methacrylic acid ester, acrylamide, styrene, styrene sulfonate, maleic anhydride, butadiene and vinyl chloride.

Referring specifically to Formula II, at least two of $R^{12}$, $R^{13}$ and $R^{14}$ are independently chosen from a group represented by halogen, preferably Cl or Br;

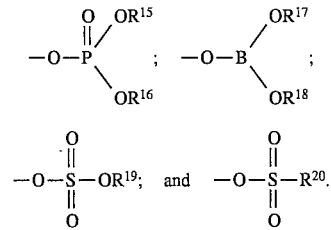

The most preferred group represented by $R^{12}$, $R^{13}$ or $R^{14}$ is chlorine or bromine. One of $R^{12}$, $R^{13}$ or $R^{14}$ can represent hydrogen; alkyl, or substituted alkyl, of 1 to 24 carbons, preferably 1 to 4 carbons; halogen; —$OR^{21}$; —$NR^{22}R^{23}$; —OM; a linking group to another triazine; sulfonamide; substituted, or unsubstituted, alkyl ether of 1 to 20 carbons; polyethylene oxide of 2 to 40 carbons; —$(OR^{24})_xR^{25}$ where x is an integer from 1 to 24; or —$L^2CR^{26}CH_2$ or a polymer thereof. Preferably one substituent chosen from $R^{12}$, $R^{13}$ and $R^{14}$ is alkyl, or substituted alkyl, of 1 to 4 carbons; a halogen chosen from Cl and Br; —$OR^{21}$; —$NR^{22}R^{23}$; —OM; a divalent linking group; sulfonamide; amino or substituted amino; substituted or unsubstituted alkyl ether of 1 to 20 carbons; polyethylene oxide of 2 to 40 carbons; —$(OR^{24})_xR^{25}$ where x is an integer from 1 to 24; or —$L^2CR^{26}CH_2$ or a polymer thereof. Most preferrably one substituent chosen from $R^{12}$, $R^{13}$ and $R^{14}$ is —OM. $R^{15}$ and $R^{16}$ independently represent sodium; potassium; ammonium; alkyl ammonium, or substituted alkyl ammonium, of 1 to 20 carbons; hydrogen; or alkyl, or substituted alkyl, of 1 to 20 carbons. Preferably $R^{15}$ and $R^{16}$ independently represent sodium; potassium; ammonium; or alkyl ammonium, or substituted alkyl ammonium, of 1 to 4 carbons. $R^{17}$ and $R^{18}$ independently represent sodium; potassium; ammonium; hydrogen; alkyl ammonium, or substituted alkyl ammonium, of 1 to 20 carbons; alkyl, or substituted alkyl, of 1 to 20 carbons. Preferably $R^{17}$ and $R^{18}$ independently represent sodium; potassium; ammonium; or alkyl ammonium of 1 to 4 carbons. $R^{19}$ and $R^{20}$ independently represent sodium; potassium; hydrogen; ammonium; alkyl ammonium, or substituted alkyl ammonium, of 1 to 20 carbons; or alkyl, or substituted alkyl, of 1 to 20 carbons. Preferably $R^{19}$ and $R^{20}$ independently represent sodium; potassium; ammonium; or alkyl ammonium of 1 to 4 carbons. $R^{21}$ represents hydrogen; alkyl, or substituted alkyl, of 1 to 20 carbons; alkoxyalkyl, or substituted alkoxyalkyl, of 1 to 40 carbons; aryl, or substituted aryl, of 6 to 40 carbons; aralkyl, or substituted aralkyl, of 7 to 41 carbons; or alkyl thioether, or substituted alkyl thioether, of 1 to 40 carbons. Preferably $R^{21}$ represents hydrogen. $R^{22}$ and $R^{23}$ independently represent hydrogen; alkyl, or substituted alkyl, of 1 to 20 carbons; aryl, or substituted aryl, of 6 to 20 carbons; alkylether, or substituted alkylether, of 1 to 20 carbons; arylether, or substituted arylether, of 6 to 20 carbons; alkylthioether, or substituted alkylthioether, of 1 to 20 carbons; arylthioether, or substituted arylthioether, of 6 to 20 carbons; sulfonyl; or alkylsulfonyl of 1 to 20 carbons. Preferably $R^{22}$ and $R^{23}$ independently represent hydrogen; sulfonyl; or alkylsulfonyl of 1 to 4 carbons. $R^{24}$ represents an ethylene or substituted ethylene. Preferably $R^{24}$ represents ethylene or isopropylene. $R^{25}$ represents an alkyl, or substituted alkyl, of 1 to 20 carbons; or an ether, or substituted ether, of 1 to 20 carbons. $R^{26}$ represents a hydrogen; or alkyl, or substituted alkyl, of 1 to 24 carbons. Preferably $R^{26}$ represents a hydrogen or methyl. $L^2$ is a divalent chemical linkage preferably chosen from a chemical bond; alkylene, or substituted alkylene, of 1 to 20 carbons; arylene, or substituted arylene, of 6 to 24 carbons; aralkyl, or substituted aralkyl, of 7 to 25 carbons; and carbonyl. Preferably $L^2$ represents a chemical bond; alkylene, or substituted alkylene, of 1 to 10 carbons; arylene, or substituted arylene, of 6 to 10 carbons; or aralkyl, or substituted aralkyl, of 7 to 12 carbons. M is a counterion. M is preferably chosen from sodium; potassium; lithium; calcium; barium; strontium; ammonium; and alkyl ammonium with 1 to 20 carbons. Most preferably M is chosen from sodium, potassium, ammonium, and alkyl ammonium of 1 to 20 carbons.

Throughout this disclosure $CH_2=CR^8$— or $CH_2=CR^{26}$— refers to an unpolymerized monomer. A polymer or copolymer formed by the polymerization or copolymerization of the vinyl group is also considered to be within the teachings of the present invention. The process of polymerization, or copolymerization is well known in the art and includes specifically radical initiated polymerization.

The recitation "atoms chosen from C, N, O, and S necessary to form a 5- or 6-membered ring" or the equivalent thereof "a 5- or 6-membered ring containing atoms chosen from a set consisting of C, N, O, and S" refers to substituted or unsubstituted rings including but not limited to: the thiazole series; e.g. thiazole, 4-methylthiazole, 4-phenylthiazole, 5-methylthiazole, 5-phenylthiazole, 4,5-dimethylthiazole, 4,5-diphenylthiazole, or 4-(2-thienyl)-thiazole;

the benzothiazole series; e.g., benzothiazole, 4-chlorobenzothiazole, 5-chlorobenzothiazole, 6-chlorobenzothiazole, 7-chlorobenzothiazole, 4-methylbenzothiazole, 5-methylbenzothiazole, 6-methylbenzothiazole, 5-bromobenzothiazole, 6-bromobenzothiazole, 4-phenylbenzothiazole, 5-phenylbenzothiazole, 4-methoxybenzothiazole, 5-methoxybenzothiazole, 6-methoxybenzothiazole, 5-iodobenzothiazole, 6-iodobenzothiazole, 4-ethoxybenzothiazole, 5-ethoxybenzothiazole, tetrahydrobenzothiazole, 5,6-dimethoxybenzothiazole, 5,6-dioxymethylenebenzothiazole, 5-hydroxybenzothiazole, or 6-hydroxybenzothiazole;

the naphthothiazole series; e.g., naphtho[1,2]-thiazole, naphtho[2,1]thiazole, 5-methoxynaphtho-[2,1]-thiazole, 5-ethoxynaphtho[2,1]thiazole, 8-methoxynaphtho[1,2]thiazole, or 7-methoxythianaphtheno-[1,2]thiazole;

the thianaphtheno-7',6',4,5-thiazole series; e.g. 4'-methoxythianaphtheno-7',6',4,5-thiazole;

the oxazole series; e.g., 4-methyloxazole, 5-methyloxazole, 4-phenyloxazole, 4,5-diphenyloxazole, 4-ethyloxazole, 4,5-dimethyloxazole, or 5-phenyloxazole;

the benzoxazole series; e.g., benzoxazole, 5-chlorobenzoxazole, 5-methylbenzoxazole, 5-phenylbenzoazole, 6-methylbenzoxazole, 5,6-dimethylbenzoxazole, 4,5-dimethylbenzoxazole, 5-methoxybenzoxazole, 5-ethoxybenzoxazole, 5-chlorobenzoxazole, 6-methoxybenzoxazole, 5-hydroxybenzoxazole, or 6-hydroxybenzoxazole;

the naphthoxazole series, e.g., naphtho[1,2]oxazole, or naphtho[2,1]oxazole;

the thiazoline series; e.g., thiazoline, or 4-methylthiazoline;

the 2-quinoline series; e.g., quinoline, 3-methylquinoline, 5-methylquinoline, 7-methylquinoline, 8-methylquinoline, 6-chloroquinoline, 8-chloroquinoline, 6-methoxyquinoline, 6-ethoxyquinoline, 6-hydroxyquinoline, or 8-hydroxyquinoline;

the 4-quinoline series; e.g., quinoline, 6-methoxyquinoline, 7-methoxyquinoline, 7-methylquinoline, or 8-methylquinoline;

the 1-isoquinoline series; e.g., isoquinoline, or 3,4-dihydroisoquinoline;

the 3-isoquinoline series; e.g., isoquinoline;

the benzimidazole series; e.g., 1,3-diethylbenzimidazole, or 1-ethyl-3-phenylbenzimidazole;

the 3,3-dialkylindolenine series; e.g., 3,3-dimethylindoline, 3,3,5-trimethylindolenine, or 3,3,7-trimethylindolenine;

the 2-pyridine series; e.g., pyridine, or 5-methylpyridine;

the 4-pyridine series;

the 3,3-dialkylbenzeindole series; e.g., 3,3-dimethylbenz[e]indole;

the tetrazole series: e.g., 1-phenyltetrazole, or 1-methyltetrazole;

the triazole series: e.g., 1-phenyl-triazole, or 1-methyltriazole;

the pyrimidine series: e.g., pyrimidine;

the thiadiazole series: e.g., 1,3,4-thiadiazole.

The terms "alkyl", "aryl", "aralkyl", "5- or 6-membered ring", "ether", "ethylene", "phenyl", "alkoxy", and "benzyl" refer to both unsubstituted and substituted groups unless specified to the contrary. Preferred substituents include halogen, nitro, carboxyl, hydroxyl, alkoxy, amine, thiol, amide, vinyl, sulfate, cyano, thioether, carboxylic acid, sulfonic acid, sulfato, and combinations thereof.

Well known in the art is the advantage of using a surfactant to assist in coating a solution. Typically the surfactant is a separate entity which is useful during coating and can be detrimental after coating is complete. By incorporating the surfactant into the chemical structure of the hardener the detrimental properties can be circumvented. A preferred embodiment of the present invention is realized when at least one of $R^1$, $R^2$, $R^3$, $R^4$, $R^5$, $R^6$, $R^7$, $R^{15}$, $R^{16}$, $R^{17}$, $R^{18}$, $R^{19}$, $R^{20}$, $R^{21}$, $R^{22}$, $R^{23}$ or one of the set consisting of $R^{12}$, $R^{13}$ and $R^{14}$ comprises a surfactant moiety incorporated into the chemical structure of the hardener. This allows a single compound to accomplish multiple tasks, namely, to act as a coating aid during the coating process after which the compound acts to crosslink the matrix as detailed above. Suitable surfactant moieties which are known in the art include alkyl chains over 6 carbons, preferably 6 to 24 carbons; polyalkyleneoxide chains such as —$(R^{27}O)_m$—, wherein $R^{27}$ is ethylene, propylene or combinations thereof and m is an integer of 1 to 30; or combinations of alkylenes and polyalkyleneoxides.

While not limited thereto, particularly preferred hardeners represented by Formula I are:

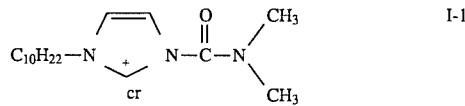

I-1

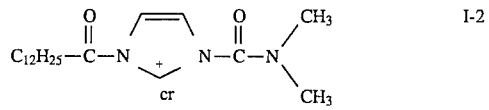

I-2

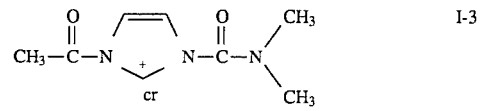

I-3

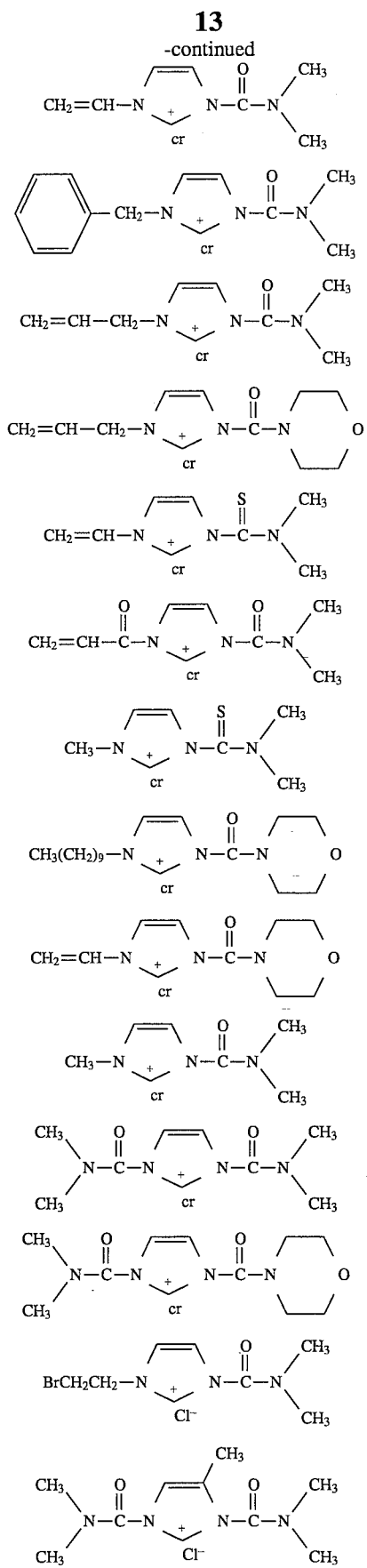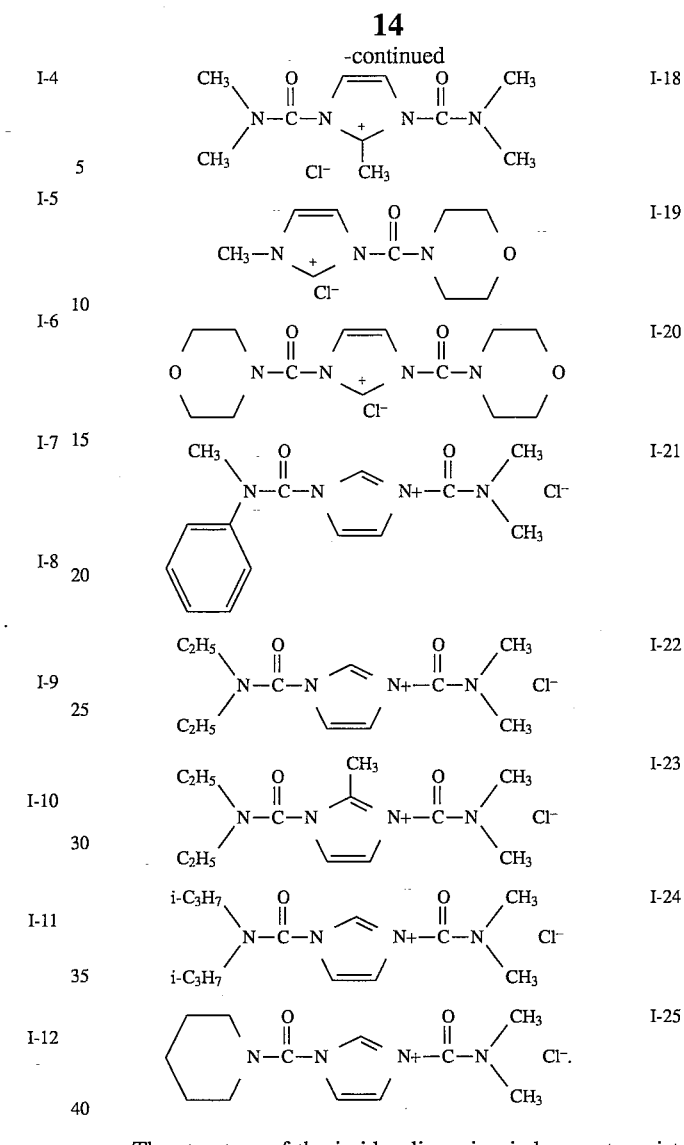
The structure of the imidazolium ring is known to exist with a delocalized charge. Comparable resonance structures can be drawn including:
While not limited thereto, particularly preferred hardeners represented by Formula II are:

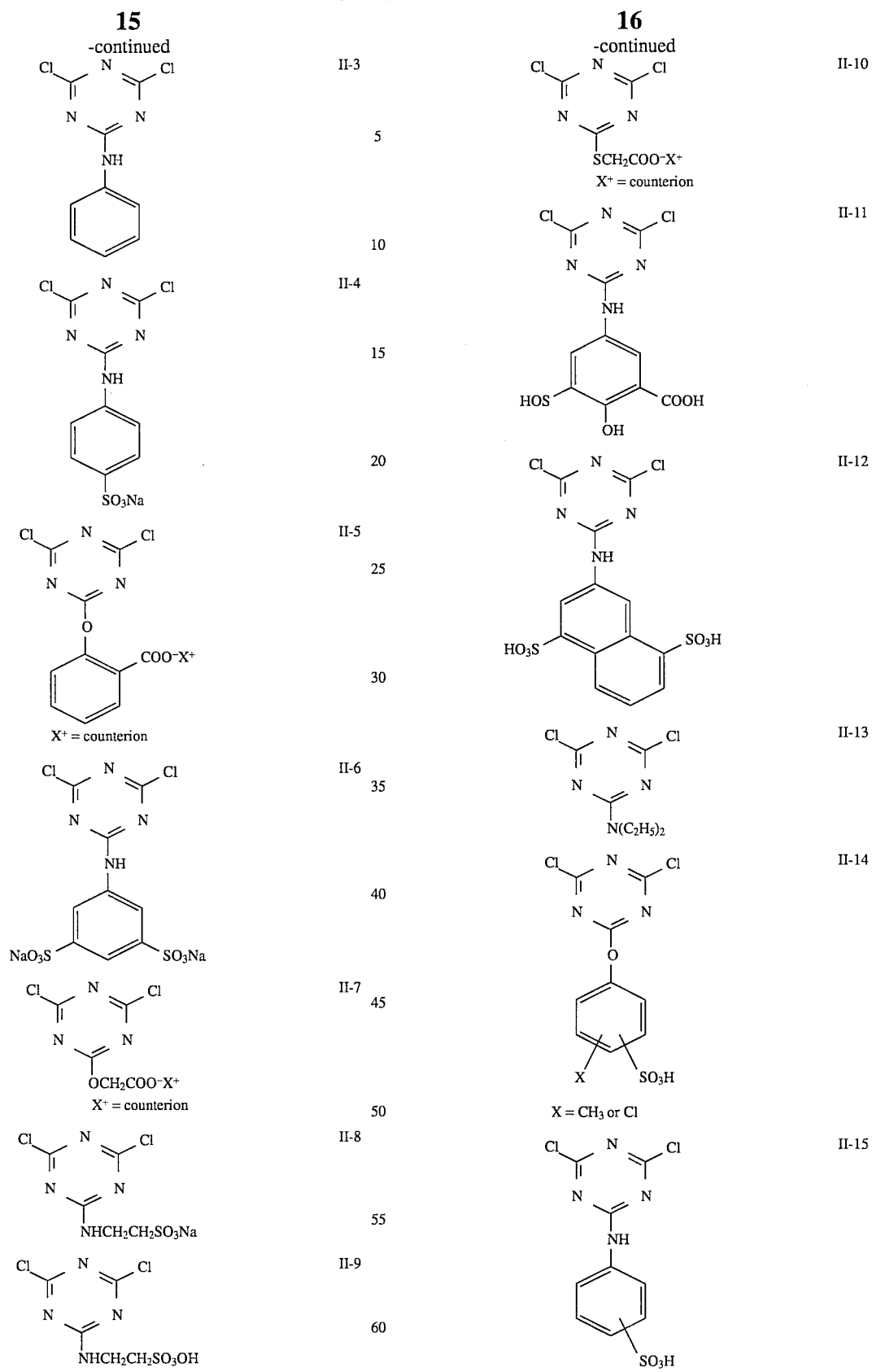

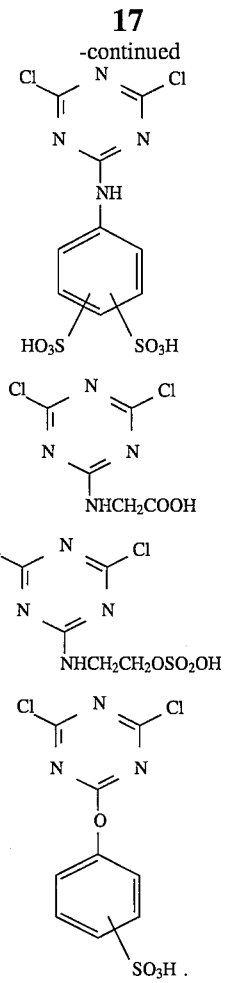

A process of hardening gelatin coatings is accomplished preferably by mixing an aqueous gelatin coating solution with an aqueous solution of the hardener just before coating.

It is particularly preferable to accomplish this mixing immediately before coating, for example, by injecting the hardener solution into a stream of the coating solution at the coating device.

The hardeners of the present invention react rapidly with a hydrophilic colloid and therefore addition of the hardener to a solution containing hydrophilic colloid must be done with care. This is particularly important in the present invention since the compounds of Formula I and Formula II are incompatible as detailed previously. The hardeners of the present invention are preferably added by injection into the coating solution as the coating solution is transported from the holding tanks to the coater. The injection time is dependent on the coater configuration but the time between injection and coating must be sufficiently long to allow thorough mixing. It is also important that the time is not so long that crosslinking and decomposition begin to occur. An addition time of no more than approximately 5 minutes prior to coating is preferred and no more than 2 minutes is most preferred. While not restricted thereto it is most preferred that the compounds of Formula I are injected into the emulsion layer of a photographic element and the compounds of Formula II are injected into an overcoat layer. Injection is accomplished by passing the coating solution past a "T" and adding the appropriate hardener solution. After the "T" the two solutions are allowed to mix sufficiently. It is most common for the coating solution to flow substantially straight through the "T" and for the hardener to be injected into the coating solution at an angle.

The photographic element of the present invention can be coated onto a substrate with any method common in the art including but not limited to curtain coating, extrusion coating, slide-bead coating and the like. Slide-bead coating is a preferred method.

Slide-bead coating is well known in the art to provide a means for supplying a flowing liquid layer or plurality of liquid layers down a slide surface to an efflux end, or lip, at which a liquid bridge, or bead, is formed in a gap between the lip and a moving substrate. The moving substrate carries away liquid from the liquid inventory in the bead in the same layered structure established on the slide. Exemplary examples include, for example, Russell, et. al., U.S. Pat. Nos. 2,761,791 and 2,761,419.

The new carbamoyl imidazolium compounds can be used alone or mixed with known hardeners, for example; triazine compounds or 2,3-dihydroxy-1,4-dioxane.

The amount of hardener solution added depends on the degree of crosslinking desired, For use in a photographic emulsion the hardener solution is typically added in an amount sufficient to equal approximately 0.01 to 1.0 mmoles of Formula I per gram of hydrophilic colloid and approximately 0.01 to 1.0 mmoles of Formula II per gram of hydrophilic colloid. More preferred is approximately 0.02 to 0.30 mmoles of the hardener represented by Formula I per gram of hydrophilic colloid and approximately 0.02 to 0.30 mmoles of the hardener represented by Formula II per gram of hydrophilic colloid. The amount added can be different for different hydrophilic colloids.

The hardeners of the present invention are most suitable for crosslinking a hydrophilic colloid layer. It is most preferred to use the hardeners of the present invention for a coated layer of hydrophilic colloid. The commercial application includes, but is not limited to, the use of a hardened hydrophilic colloid layer in a photographic element as either a photosensitive layer, an underlayer, an overcoat layer or a dyed layer.

The process of hardening gelatin coatings according to the invention is used preferably for hardening gelatin-containing coatings that are components of photographic recording materials. These can be light-sensitive silver halide emulsion coatings that contain, for example, unsensitized emulsions, orthochromatic, panchromatic, or infrared-sensitive emulsions, emulsions containing color couplers, x-ray emulsions, or ultrahigh contrast emulsions for reprography. The hardened gelatin coatings can be protective coatings, filter coatings, antihalation coatings, anticurl coatings, or photographic auxiliary coatings in general. Photographic recording materials, particularly those for color photography, usually contain several such coatings.

A photosensitive layer typically comprises silver halide dispersed in a hydrophilic colloid binder. The silver halide is optionally chemically and optionally spectrally sensitized as known in the art and the layer can contain other adjuvants such as dyes, stabilizers, development agents, color coupling agents, toners, surfactants, and the like.

An underlayer typically comprises a hydrophilic colloid layer with an optional dye dispersed therein. The overcoat is typically coated as the outermost layer to protect the photosensitive layer from abrasion and the like. The overcoat layer can comprise dyes, surfactants, or other adjuvants as known in the art.

The term "hydrophilic colloid" or its homologues "gelatin" and "proteinaceous material" are used herein to refer to protein substances which are derived from collagen. In the context of the present invention "hydrophilic colloid" also refers to substantially equivalent substances such as synthetic analogues of gelatin. Generally gelatin is classified as alkaline gelatin, acidic gelatin or enzymatic gelatin. Alkaline gelatin is obtained from the treatment of collagen with a base such as calcium hydroxide. Acidic gelatin is that which is obtained from treatment of collagen in acid such as hydrochloric acid. Enzymatic gelatin is generated with a hydrolase treatment of collagen. The teachings of the present invention are not restricted to gelatin type or a molecular weight of the gelatin.

To harden several coatings superimposed upon one another on one side of a support in photographic recording materials, the hardener is added preferably only to one layer, for example, an undercoat or overcoat, which itself can be without gelatin. This can also be an auxiliary layer, for example, in the process according to Reif, U.S. Pat. No. 5,034,249. It is also possible to coat a solution containing hardener subsequently in a special process step onto the layers containing gelatin.

Another preferred use of the compounds of the invention is as peptide coupling reagents, for example, in the synthesis of polypeptides or to anchor polypeptides such as gelatin on surfaces or on soluble polymers containing carboxylic acid functions.

The new carbamoyl imidazolium compounds can be prepared simply and from easily available starting materials. They harden as rapidly as known instant hardeners, but are substantially more stable as solids and in aqueous solution. The solids, their solutions, and gelatin coatings hardened by them are free of annoying and harmful odors.

The invention can be used to harden all types of gelatin coatings, for example, in preparing protective coatings on objects, coatings containing reactive materials for analytical or diagnostic purposes, but particularly the light-sensitive coatings and auxiliary coatings on photographic recording materials.

The film support for the emulsion layers used in the novel process can be any suitable transparent plastic. For example, the cellulosic supports, e.g., cellulose acetate, cellulose triacetate, cellulose mixed esters, etc., can be used. Polymerized vinyl compounds, e.g., copolymerized vinyl acetate and vinyl chloride, polystyrene, and polymerized acrylates can also be used. Preferred film supports include those formed from the polyesterification product of a dicarboxylic acid and a dihydric alcohol made according to the teachings of Alles, U.S. Pat. No. 2,779,684 and the patents referred to in the specification thereof. Other suitable supports are polyethylene terephthalate/isophthalates of British Patent 766,290 and Canadian Patent 562,672 and those obtainable by condensing terephthalic acid and dimethyl terephthalate with propylene glycol, diethylene glycol, tetramethylene glycol or cyclohexane 1,4-dimethanol (hexahydro-p-xylene alcohol). Films of Bauer et al., U.S. Pat. No. 3,052,543 can also be used. The above polyester films are particularly suitable because of their dimensional stability.

Meltpoint was measured by observing the melting temperature in 0.1M NaOH for a hardened gelatin coating. Melt time was measured by observing the time, in minutes, required for the hardened layer to dissolve in a 1.5% NaOH solution at 50° C. Water absorption was determined by weighing a dry 10 cm×10 cm film sample, submerging the sample for 30 minutes in an aqueous solution buffered to a pH of approximately 10.0 by a borate buffer, allowing the excess water on the surface to drain off of the film, and weighing the swollen film. Water absorption (WA) is defined as the weight gain per surface unit or as a percentage according the the equation:

$$\% \; WA = \frac{\text{Wet weight(mg)} - \text{Dry weight(mg)}}{\text{Dry Weight(mg)}} \times 100$$

Wet gouge is a measure of the strength of the binder under processing conditions and is measured by dragging a stylus which increases force with distance over a film submerged in a mock developer solution comprising all ingredients except hydroquinone and phenidone. The wet gouge is then determined as the distance traversed by the stylus prior to destruction of the film surface. A larger distance indicates a stronger matrix.

SYNTHESIS OF HARDENERS OF FORMULA I

The imidazolium compounds of the invention can be produced by various synthesis procedures. Therefore, an optimum method can be selected for preparing a specific compound.

The synthesis is usually started with an imidazole compound and has two steps, whereby the imidazole is reacted first with an equivalent of a carbamoyl chloride and the resulting intermediate product is then reacted with another equivalent of the same or a different carbamoyl chloride. Thus, symmetrical or asymmetrical compounds can be obtained.

As an example, imidazole can be reacted in the presence of an acid scavenger, for example, triethylamine, with an equivalent of an N,N-dialkyl carbamoyl chloride. The preferred solvents for this are acetone and tetrahydrofuran. Triethyl ammonium chloride salt is precipitated and an intermediate product in the separated solution can be reacted with another equivalent of a dialkyl carbamoyl chloride to obtain a bis-carbamoyl compound. This crystallizes in a form sufficiently pure to use and can be easily filtered out.

The intermediate product can also be obtained by the reaction of sodium imidazole with an equivalent of a carbamoyl chloride in a polar solvent, for example, tetrahydrofuran, separating precipitated sodium chloride, and as above, processing further in the solution to the bis-carbamoyl compound.

Another possibility for preparing the monocarbamoyl imidazole intermediate product is reacting a carbonyl diimidazole with an equivalent of a secondary amine. Before further reaction, the intermediate product must be isolated and recrystallized to remove the imidazole formed in the first step.

1,3-bis-(dimethylcarbamoyl)-imidazolium chloride (I-14)

10.75 g (0.1 mole) dimethylcarbamoyl chloride are added dropwise with stirring to a solution of 6.8 g. (0.1 mole) imidazole and 11 g. triethylamine in 70 ml dry acetone. On warming, triethyl- ammonium chloride precipitates. After 5 hours standing at room temperature, the reaction mixture is filtered and 10.75 g. dimethyl- carbamoyl chloride is added again to the filtrate. After 2 days at room temperature, the crystalline product is filtered off, washed with acetone, and vacuum dried. Yield: 20.2 g 1,3-bis-(dimethylcarbamoyl)-imidazolium chloride (77% of theoretical), melting point 115° C. Analysis:

Calculated: C 43.8% H 6.08% N 22.7%.

Found: C 43.7% H 6.2% N 22.8%.

1,3-bis-(morpholinocarbonyl)-imidazolium chloride (I-20)

7.5 g. (0.05 mole) morpholino-4-carbonyl chloride are added to a solution of 3.4 g. (0.05 mole) imidazole and 5.5 g. triethylamine in 60 ml dry tetrahydrofuran. The mixture is stirred 30 minutes at 50° C. The precipitated triethyl-ammonium chloride is filtered off. An additional 7.5 g morpholino-4-carbonyl chloride are added to the filtrate. After standing 2 days at room temperature, crystals of 1,3-bis-(morpholinocarbonyl)imidazolium chloride separate, are filtered off, washed with ether and vacuum dried. Yield: 9.6 g (58% of theoretical), melting point 116° C.
Analysis:

Calculated: C 48.1% H 6.9% N 20.4%.

Found: C 48.0% H 7.0% N 20.6%.

Standard organic reaction synthetic procedures can be employed as known in the art. While other synthetic procedures can be employed, the hardeners of Formula I were prepared in a consistent manner according to the following procedure. The appropriate N-substituted imidazol (0.2 mol) and the appropriate carbonyl chloride, or thiocarbomyl chloride (0.2 mol) were dissolved in 100 ml. of acetone and refluxed for approximately 2 hrs. The reaction mixture was cooled to precipitate the product which was then recovered by filtration. The filtrate was rinsed with acetone and dried in a dessicator at ambient conditions.

1-decyl-3-dimethylcarbamoylimidazolium bromide (I-1).

To 13.6 gm (0.2 mole) of imidazole (Aldrich Chemical Co., Milwaukee, Wis., 99%) and 20.2 gm of triethylamine (Aldrich, 99%) in 100 ml dry acetone (Fisher Scientific Co., Pittsburgh, Pa.) in a magnetically stirred 250 ml round bottom flask under dry nitrogen was added. 21.5 gm (0.2 mole) dimethylcarbamyl chloride (Aldrich, 99%) dropwise over a 20 min. period from a side-arm pressure equalizing addition funnel. A white precipitate formed during the addition under conditions of mild exothermicity. The addition funnel was replaced with a reflux condensor and the reaction refluxed for a further one hour. After cooling to room temperature, the precipitate was isolated by Buchner filtration onto Wattman #1 paper, rinsed on the filter with acetone, and discarded. The combined filtrate and rinse acetone solution was divided into two equal parts, each containing 0.1 mole of 1-dimethylcarbamoylimidazole. To one of these parts was added 22.1 gm (0.1 mole) of 1-bromodecane (Aldrich 98%) and the solution refluxed for seven hours under dry nitrogen. The acetone was evaporated at water aspirator vacuum in a rotoevaporator to the point where two layers formed. The upper layer contained largely unreacted bromodecane and the lower yielded 12 gm (0.043 mole for a 21.4% theorical yield) of the imidazolium salt as a waxy solid upon cooling to 5° C. The purity and identity of this product was confirmed by proton and carbon NMR in deuterium oxide solution.

SYNTHETIC PROCEDURE FOR HARDENERS OF FORMULA II 2,4-dichloro-6-hydroxy-1,3,5-triazine, sodium, salt (II-1)

1215 g of sodium phosphate tribasic was added to 70000 g. of water. The mixture was cooled to 24° C. and stirred until the sodium phosphate dissolved. 5000 g. of cyanuric chloride was added slowly. The pH was maintained between 8.0 and 9.5 with 1N NaOH. After reaction is complete the pH is adjusted to approximately 7.8. The pH should not be allowed to drop below 7.7 at any time during the preparation or storage since rapid decomposition will commence.

ILLUSTRATIVE EXAMPLES

In the Examples below, the following comparison compounds are used:

V-1: Dimethyl carbamoyl pyridinium chloride

V-2: Morpholino carbonyl pyridinium chloride

V-3: 1-Morpholinocarbonyl-(pyridinium-4-ethanesulfonate)NaCl.

EXAMPLE 1

An anionic surfactant and 1% by weight (relative to the gelatin) of a dispersed copper phthalocyanine pigment are added to a 5% aqueous solution of a photographic gelatin. Portions of this solution were mixed with the hardeners listed in Table 1 (0.1 millimole per gram gelatin in each case) in the form of freshly prepared solutions of about 5% by weight and distributed by a doctor blade on polyethylene terephthalate sheets to make coatings about 60 microns thick.

After drying one hour at room temperature, samples of the resulting films were immersed in 60° C. water and tested for odor. Other samples were hung in 0.5N sodium hydroxide solution at 25° C. The sodium hydroxide solution was warmed at 1° K./min and the temperature at which the gelatin layer started to melt was noted. This test was repeated after the films were stored 2 days and 10 days.

TABLE 1

| Hardener | Start of Melting (°C.) After Storage for | | | Odor |
| | 1 Hour | 2 Days | 10 Days | |
| --- | --- | --- | --- | --- |
| I-14 | 50 | 55 | 55 | None |
| I-15 | 48 | 55 | 55 | None |
| I-20 | 44 | 50 | 51 | None |
| I-22 | 50 | 55 | 56 | None |
| I-23 | 38 | 54 | 58 | None |
| V-1 | 56 | 60 | 61 | Pyridine |
| V-2 | 50 | 56 | 58 | Pyridine |

The results show that the compounds of the invention and comparison compounds V-1 and V-2 act as instant hardeners, that is, the temperature at which melting started increased close to its final value after one hour and hardening was just about complete after 2 days.

EXAMPLE 2

A gelatin/silver halide emulsion and a gelatin solution overcoating were coated simultaneously on a support. The gelatin quantities in the emulsion and overcoating were 4:1. An aqueous solution of a hardener listed in Table 2 was added to the overcoating solution 5 minutes before coating. The quantity of hardener was in all cases 0.1 millimole per gram of total gelatin in the emulsion and overcoating. The test was conducted with freshly prepared hardener solution and with solution stored 2 days at room temperature.

One hour after coating, the films were processed in a developer with the composition indicated below at 36° C. and a developing time of 40 sec in a commercial developing machine and fixed in a commercial fixing bath containing an aluminum salt.

| DEVELOPER COMPOSITION | |
| --- | --- |
| Water | 600 mL |
| Potassium hydroxide | 30 gm |
| Potassium disufate | 66 gm |
| EDTA | 3 gm |
| Potassium bromide | 3 gm |
| Benzotriazole | 0.5 gm |
| Phenyl mercaptotetrazole | 0.05 gm |
| Hydroquinone | 25 gm |

-continued

| DEVELOPER COMPOSITION | |
|---|---|
| N-methyl-p-aminophenol sulfonate | 1.5 gm |
| Sodium carbonate monohydrate | 48 gm |
| Diethylamino propanediol | 25 gm |
| pH adjusted to | 10.9 at 20° C. |
| Water to make | 1 L |

The machine processibility of the test films was judged as follows:

Yes, if the fixed and dried film was clear and had a smooth, glossy surface;

No, if the film was cloudy with a matte surface or the emulsion layer was wholly or partially dissolved away.

TABLE 2

| Sample | Hardener | Age of Hardener Solution | Machine Processibility |
|---|---|---|---|
| 1 | I-14 | Fresh | Yes |
| 2 | I-14 | 2 Days | Yes |
| 3 | V-1 | Fresh | Yes |
| 4 | V-1 | 2 Days | Yes |
| 5 | V-2 | Fresh | Yes |
| 6 | V-2 | 2 Days | No |
| 7 | V-3 | Fresh | Yes |
| 8 | V-3 | 2 Days | No |

These results show that the aged solutions of the comparison materials V-2 and V-3 do not have a satisfactory hardening effect to assure machine processibility of the films. In contrast, the aged solution of material I-14 of the invention is at least as good as the best of the comparison materials, V-1.

EXAMPLE 3

A 0.25 molar aqueous solution of each hardener listed in Table 3 was prepared and the content of active material was determined by ultraviolet photometry on diluted samples after the solutions were stored for various times at 20° C. The results show the superior stability of compound I-14 of the invention even when compared to the most stable comparison material V-1.

TABLE 3

| Hardener | Solution Content as Percent of Starting Value after | | | |
|---|---|---|---|---|
| | 0 Hours | 10 Hours | 2 Days | 7 Days |
| I-14 | 100 | 100 | 100 | 100 |
| V-1 | 100 | 95 | 88 | 60 |
| V-2 | 100 | 50 | <10 | 0 |

Examples 1–3 illustrate the stability advantage of hardeners of Formula I. Subsequent addition of hardeners of Formula II provide even greater advantages as illustrated in Examples 4–6.

EXAMPLE 4

A photographic emulsion was prepared as known in the art. The emulsion comprised tabular silver halide grains and 70 grams of gelatin per mole of silver halide. The emulsion was coated on a subbed polyethylene terephthalate support to a silver coating weight of approximately 4.8 g/M$^2$. The combinations of hardeners listed in Table 4 were added either as a 2% solution (hardener I) or as a 10% solution (hardener II). In the examples Hardener I was added to the emulsion and Hardener II was added to the overcoat. The samples were held for approximately 1 week and analyzed yielding the results provided in Table 4.

TABLE 4

Physical Properties of Gelatin Layer Crosslinked with Inventive Hardeners

| Hardener I | | Hardener II | | | |
|---|---|---|---|---|---|
| Hardener | Amount | Hardener | Amount | MT | |
| HCHO | 20.0 | — | — | 3 | Control |
| HCHO | 30.0 | — | — | 15 | Control |
| HCHO | 40.0 | — | — | 24 | Control |
| I-14 | 5.0 | — | — | 3 | Inventive |
| I-14 | 10.0 | — | — | 6 | Inventive |
| I-14 | 15.0 | — | — | 12 | Inventive |
| I-14 | 20.0 | — | — | 18 | Inventive |
| — | — | II-1 | 5.0 | 3 | Control |
| I-14 | 5.0 | II-1 | 5.0 | 6 | Inventive |
| I-14 | 10.0 | II-1 | 5.0 | 12 | Inventive |
| I-14 | 15.0 | II-1 | 5.0 | 15 | Inventive |
| I-14 | 20.0 | II-1 | 5.0 | 18 | Inventive |
| — | — | II-1 | 15.0 | 6 | Control |
| I-14 | 5.0 | II-1 | 15.0 | 9 | Inventive |
| I-14 | 10.0 | II-1 | 15.0 | 12 | Inventive |
| I-14 | 15.0 | II-1 | 15.0 | 15 | Inventive |
| I-14 | 20.0 | II-1 | 15.0 | 21 | Inventive |
| — | — | II-1 | 20.0 | 6 | Control |
| I-14 | 5.0 | II-1 | 20.0 | 9 | Inventive |
| I-14 | 10.0 | II-1 | 20.0 | 12 | Inventive |
| I-14 | 15.0 | II-1 | 20.0 | 18 | Inventive |
| I-14 | 20.0 | II-1 | 20.0 | 33 | Inventive |

Amount of hardener is listed as mmoles of hardener per 200 grams of gelatin. MT represents the melt time in minutes in 1.5 wt % NaOH at 50° C. The data demonstrates an increase in the crosslinking of the hydrophilic colloid binder as indicated by the increased MT observed with combinations of hardeners.

EXAMPLE 5

An emulsion substantially similar to that used in Example 4 was prepared. Various hardener levels were added to individual aliquots as recorded in Table 5. The melt time (MT) and water absorption (WA mg/cm$^2$) were measured after approximately 1 month and recorded in Table 5.

TABLE 5

Physical Properties of Gelatin Layer Crosslinked with Inventive Hardeners

| Hardener I | | Hardener II | | | | |
|---|---|---|---|---|---|---|
| Hardener | Amount | Hardener | Amount | MT | WA | |
| I-14 | 10.0 | — | — | 3 | .60 | Inventive |
| I-14 | 20.0 | — | — | 9 | .44 | Inventive |
| I-14 | 30.0 | — | — | 15 | .39 | Inventive |
| I-14 | 40.0 | — | — | 22 | .35 | inventive |
| — | — | II-1 | 10.0 | 3 | .56 | Control |
| I-14 | 10.0 | II-1 | 10.0 | 9 | .42 | Inventive |
| I-14 | 20.0 | II-1 | 10.0 | 18 | .38 | Inventive |
| I-14 | 30.0 | II-1 | 10.0 | 24 | .35 | Inventive |
| I-14 | 40.0 | II-1 | 10.0 | 33 | .31 | Inventive |
| — | — | II-1 | 20.0 | 15 | .41 | Control |
| I-14 | 10.0 | II-1 | 20.0 | 18 | .38 | Inventive |
| I-14 | 20.0 | II-1 | 20.0 | 22 | .37 | Inventive |
| I-14 | 30.0 | II-1 | 20.0 | 28 | .33 | Inventive |
| I-14 | 40.0 | II-1 | 20.0 | 37 | .31 | Inventive |
| — | — | II-1 | 30.0 | 24 | .39 | Control |
| I-14 | 10.0 | II-1 | 30.0 | 25 | .37 | Inventive |

TABLE 5-continued

Physical Properties of Gelatin Layer Crosslinked with Inventive Hardeners

| Hardener I | | Hardener II | | | | |
|---|---|---|---|---|---|---|
| Hardener | Amount | Hardener | Amount | MT | WA | |
| I-14 | 20.0 | II-1 | 30.0 | 34 | .32 | Inventive |
| I-14 | 30.0 | II-1 | 30.0 | 34 | .32 | Inventive |
| I-14 | 40.0 | II-1 | 30.0 | 42 | .30 | Inventive |
| — | — | II-1 | 40.0 | 37 | .39 | Control |
| I-14 | 10.0 | II-1 | 40.0 | 33 | 35 | Inventive |
| I-14 | 20.0 | II-1 | 40.0 | 43 | 35 | Inventive |
| I-14 | 30.0 | II-1 | 40.0 | 46 | .34 | Inventive |
| I-14 | 40.0 | II-1 | 40.0 | 49 | .31 | Inventive |

The data of Table 5 indicates that the amount of water absorbed is lower when the combination of hardeners are used and the crosslinking is higher as indicated by the melt time.

EXAMPLE 6

An emulsion substantially similar to that described in Example 1 was prepared, The hardener levels are recorded in Table 6, In Table 6 % WP represents the amount of water absorbed as a percentage of the total weight of the film; MT is the melt time in minutes; and WG is wet gouge in granms.

TABLE 6

Physical Properties of Gelatin Layer Crosslinked with Inventive Hardeners

| Hardener I | | Hardener II | | | | |
|---|---|---|---|---|---|---|
| Hardener | Amount | Hardener | Amount | % WA | MT | WG |
| II-14 | 10.0 | II-1 | 4.1 | 14 | 7 | 4 |
| II-14 | 10.0 | — | — | 16 | 4 | 0 |
| — | — | II-1 | 4.1 | 17 | 3 | 0 |
| II-14 | 20.0 | II-1 | 8.2 | 13 | 19 | 3.5 |
| II-14 | 20.0 | — | — | 15 | 13 | 1.5 |
| — | — | II-1 | 8.2 | 15 | 3 | 0 |

In every case when the combination of hardeners is employed the film crosslinking is higher than the control examples. The amount of crosslinking is indicated by the MT or WG. The water absorption of the inventive samples is lower than the controls, as indicated by % WA.

The combined results of Examples 4–6 indicate that the additive effect of the hardeners can be appreciated without degradation of either.

Examples 1–3 indicate that the imidazolium hardeners of Formula I are more stable than currently available peptide couplers and that they provide a film with improved machine processability, Examples 4–6 illustrate the synergism which occurs when the hardeners of Formula I and the hardeners of Formula II are used concurrently.

We claim:

1. A photographic element comprising a silver halide containing photosensitive layer wherein a first hydrophilic colloid layer is hardened with 0.01 to 1.0 millimoles per gram of hydrophilic colloid of at least one imidazolium compound of formula:

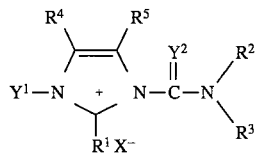

wherein:

$Y^1$ is an alkyl of 1 to 24 carbons; aryl of 6 to 24 carbons; aralkyl of 7 to 25 carbons; a 5- or 6-membered ring containing atoms chosen from the group consisting of C, N, O, and S; —$L^1CR^8CH_2$ or a polymer thereof; —$C(Y^4)E$; or

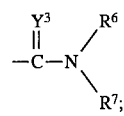

E is an alkyl of 1 to 24 carbons; aryl of 6 to 24 carbons; aralkyl of 7 to 25 carbons; —$OR^9$; —CN; or a 5- or 6-membered ring containing atoms chosen from the group consisting of C, N, O, and S;

$L^1$ is a linking group;

$R^1$ is hydrogen; alkyl of 1 to 24 carbons; aryl of 6 to 24 carbons; aralkyl of 7 to 25 carbons; —$OR^{10}$; halogen; nitro; carboxyl; mercapto; alkylamino of 1 to 24 carbons; or a 5- or 6-membered ring containing atoms chosen from the group consisting of C, N, O, and S;

$R^2$ and $R^3$ independently represent hydrogen; alkyl of 1 to 24 carbons; aryl of 6 to 24 carbons; or aralkyl of 7 to 25 carbons; or $R^2$ and $R^3$ independently represent, or are taken together to represent, a 5- or 6-membered ring containing atoms chosen from the group consisting of C, N, O, and S;

$R^4$ and $R^5$ independently represent hydrogen; alkyl of 1 to 24 carbons; aryl of 6 to 24 carbons; aralkyl of 7 to 25 carbons; nitro; carboxyl; mercapto; —$OR^{11}$; halogen; alkylamino of 1 to 24 carbons; or a 5- or 6-membered ring containing atoms chosen from the group consisting of C, N, O, and S; or $R^4$ and $R^5$ taken together represent a 5- or 6-membered ring containing atoms chosen from the group consisting of C, N, O, and S;

$X^-$ is a counterion;

$Y^2$, $Y^3$ and $Y^4$ independently represent O or S;

$R^6$ and $R^7$ independently represent hydrogen; alkyl of 1 to 24 carbons; aryl of 6 to 24 carbons; aralkyl of 7 to 25 carbons; or a 5- or 6-membered ring containing atoms chosen from the group consisting of C, N, O, and S; or $R^6$ and $R^7$ taken together represent the atoms chosen from C, N, O and S necessary to form a 5- or 6-member ring;

$R^8$ represents a hydrogen; alkyl of 1 to 24 carbons; —$C(O)R^{28}$; —CN; or aryl of 6 to 24 carbons;

$R^9$ represents hydrogen; alkyl of 1 to 24 carbons; or aryl of 6 to 24 carbons;

$R^{10}$ and $R^{11}$ independently represent hydrogen or alkyl of 1 to 5 carbons; and $R^{28}$ represents hydrogen; alkyl of 1 to 24 carbons; alkoxy of 1 to 24 carbons; amine; or alkylamine of 1 to 24 carbons.

2. The photographic element of claim 1, wherein said imidazolium compound is:

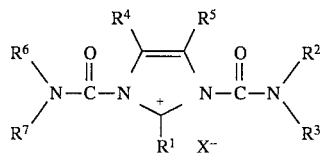

wherein
- $R^2$ and $R^3$ each independently represent alkyl of 1–3 carbon atoms, a phenyl group, or a benzyl group; or $R^2$ and $R^3$ taken together form a five or six member saturated ring having 1 or 2 nitrogen atoms and 0 or 1 oxygen atom, and one of the nitrogen atoms is unsubstituted or substituted with a methyl, ethyl, or propyl group;
- $R^6$ and $R^7$ each independently represent alkyl of 1–3 carbon atoms, a phenyl group, or a benzyl group; or $R^6$ and $R^7$ taken together form a five or six member saturated ring having 1 or 2 nitrogen atoms and 0 or 1 oxygen atom, and one of the nitrogen atoms is unsubstituted or substituted with a methyl, ethyl, or propyl group;
- R1, R4 and R5 independently are hydrogen or an alkyl group with 1–3 carbon atoms; and
- $X^-$ is an anion.

3. The photographic element of claim 1, wherein said imidazolium compound is present in a range of 0.02 to 0.3 millimole per gram of said hydrophilic colloid.

4. The photographic element of claim 1, further comprising a support; and said imidazolium compound is present in only one of several hydrophilic colloid layers on said support.

5. The photographic element of claim 1, wherein in said at least one imidazolium compound:
- Y2 represents O;
- $R^1$ is hydrogen; alkyl of 1 to 24 carbons; aryl of 6 to 24 carbons; aralkyl of 7 to 25 carbons; or halogen;
- $R^2$ and $R^3$ independently represent hydrogen; alkyl of 1 to 24 carbons; aryl of 6 to 24 carbons; aralkyl of 7 to 25 carbons; or a 5- or 6-membered ring containing atoms chosen from a set consisting of C, N, O, and S; or $R^2$ and $R^3$ taken together represent a 5- or 6-membered ring containing atoms chosen from a set consisting of C, N, O, and S;
- $Y^1$ is

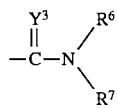

wherein $Y^3$ is O; and
- $R^6$ and $R^7$ independently represent hydrogen; alkyl of 1 to 24 carbons; aryl of 6 to 24 carbons; aralkyl of 7 to 25 carbons; or a 5- or 6-membered ring containing atoms chosen from a set consisting of C, N, O, and S; or $R^6$ and $R^7$ taken together represent a 5- or 6-membered ring containing atoms chosen from a set consisting of C, N, O, and S.

6. The photographic element of claim 5, wherein said at least one imidazolium compound is chosen from a set consisting of:

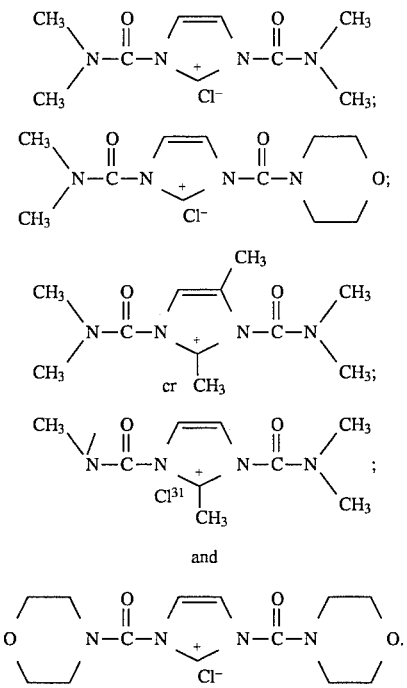

7. The photographic element of claim 1, wherein in said at least one imidazolium compound:
- $Y^1$ is an alkyl of 1 to 24 carbons; aryl of 6 to 24 carbons; a 5- or 6-membered ring containing atoms chosen from a set consisting of C, N, O, and S; or —$L^1CR^8CH_2$ or a polymer thereof;
- $L^1$ is a linking group; and
- $R^8$ represents a hydrogen; or an alkyl of 1 to 3 carbons.

8. The photographic element of claim 7, wherein said at least one imidazolium compound is chosen from a set consisting of:

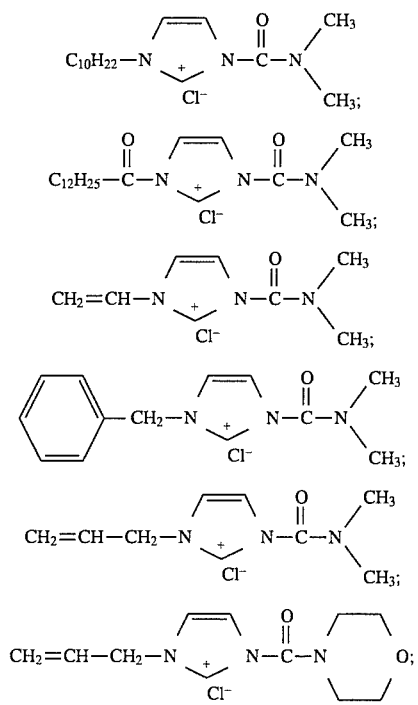

29
-continued

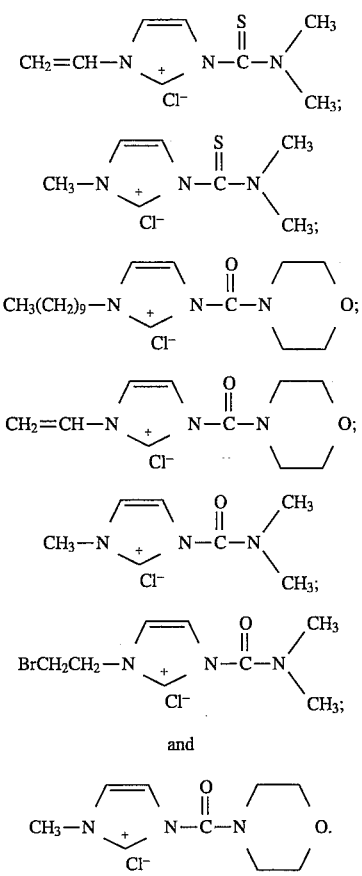

9. The photographic element of claim 1 further comprising a second hydrophilic colloid layer hardened by at least one triazine compound of formula:

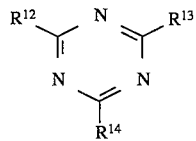

wherein:
at least two of $R^{12}$, $R^{13}$ and $R^{14}$ are independently chosen from a set consisting of halogen;

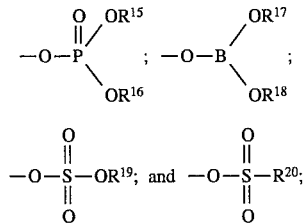

one of $R^{12}$, $R^{13}$ and $R^{14}$ represents hydrogen; alkyl of 1 to 24 carbons; halogen; —$OR^{21}$; —$NR^{22}R^{23}$; —OM; a divalent linking group to another triazine compound; sulfonamide; alkylether of 1 to 20 carbons; polyethylene oxide of 2 to 40 carbons; —$(OR^{24})_xR^{25}$; or —$L^2CR^{26}CH_2$ or a polymer thereof;

$R^{15}$ and $R^{16}$ independently represent sodium; potassium; ammonium; alkyl ammonium of 1 to 20 carbons; hydrogen; or alkyl of 1 to 20 carbons;

30

$R^{17}$ and $R^{18}$ independently represent sodium; potassium; ammonium; hydrogen; alkyl ammonium of 1 to 20 carbons; or alkyl of 1 to 20 carbons;

$R^{19}$ and $R^{20}$ independently represent sodium; potassium; hydrogen; ammonium; alkyl ammonium of 1 to 20 carbons; or alkyl of 1 to 20 carbons;

$R^{21}$ represents hydrogen; alkyl of 1 to 20 carbons; alkoxyalkyl of 1 to 40 carbons; aryl of 6 to 40 carbons; aralkyl of 7 to 41 carbons; or alkylthioether of 1 to 40 carbons;

$R^{22}$ and $R^{23}$ independently represent hydrogen; alkyl of 1 to 20 carbons; aryl of 6 to 20 carbons; alkylether of 1 to 20 carbons; arylether of 6 to 20 carbons; alkylthioether of 1 to 20 carbons; arylthioether of 6 to 20 carbons; sulfonyl; or alkylsulfonyl of 1 to 20 carbons;

$R^{24}$ represents an ethylene;

$R^{25}$ represents an alkyl of 1 to 20 carbons; or an ether of 1 to 20 carbons;

$R^{26}$ represents a hydrogen or alkyl of 1 to 24 carbons;

$L^2$ is a chemical linkage;

M is a counterion; and x is an integer from 1 to 24.

10. The photographic element of claim 9, wherein at least two of $R^{12}$, $R^{13}$ and $R^{14}$ are halogen;

one of $R^{12}$, $R^{13}$ and $R^{14}$ is —$OR^{21}$; —$NR^{22}R^{23}$; —OM; a divalent linking group; sulfonamide; or amino;

$R^{21}$ represents hydrogen, alkyl of 1 to 20 carbons; alkoxyalkyl of 1 to 40 carbons; aryl of 6 to 10 carbons; aralkyl of 7 to 41 carbons; or alkyl thioether of 1 to 40 carbons;

$R^{22}$ and $R^{23}$ independently represent hydrogen; alkyl of 1 to 20 carbons; aryl of 6 to 20 carbons; alkyl ether of 1 to 20 carbons; aryl ether of 6 to 20 carbons; alkyl thioether of 1 to 20 carbons; aryl thioether of 6 to 20 carbons; sulfonyl; or alkyl sulfonyl of 1 to 20 carbons;

$R^{24}$ represents an ethyl or substituted ethyl;

$R^{25}$ represents an alkyl of 1 to 20 carbons; or an ether or 1 to 20 carbons;

$R^{26}$ represents a hydrogen; or alkyl of 1 to 24 carbons;

$L^2$ is a chemical linkage;

M is a counterion chosen from a set consisting of sodium, potassium, lithium, calcium, barium, strontium, ammonium, and alkyl ammonium with 1 to 20 carbons; and x is an integer from 1 to 24.

11. The photographic element of claim 10, wherein said at least one triazine compound is chosen from a set consisting of:

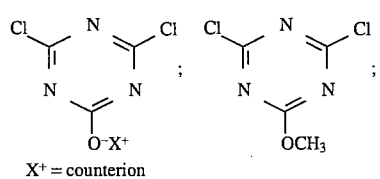

$X^+$ = counterion

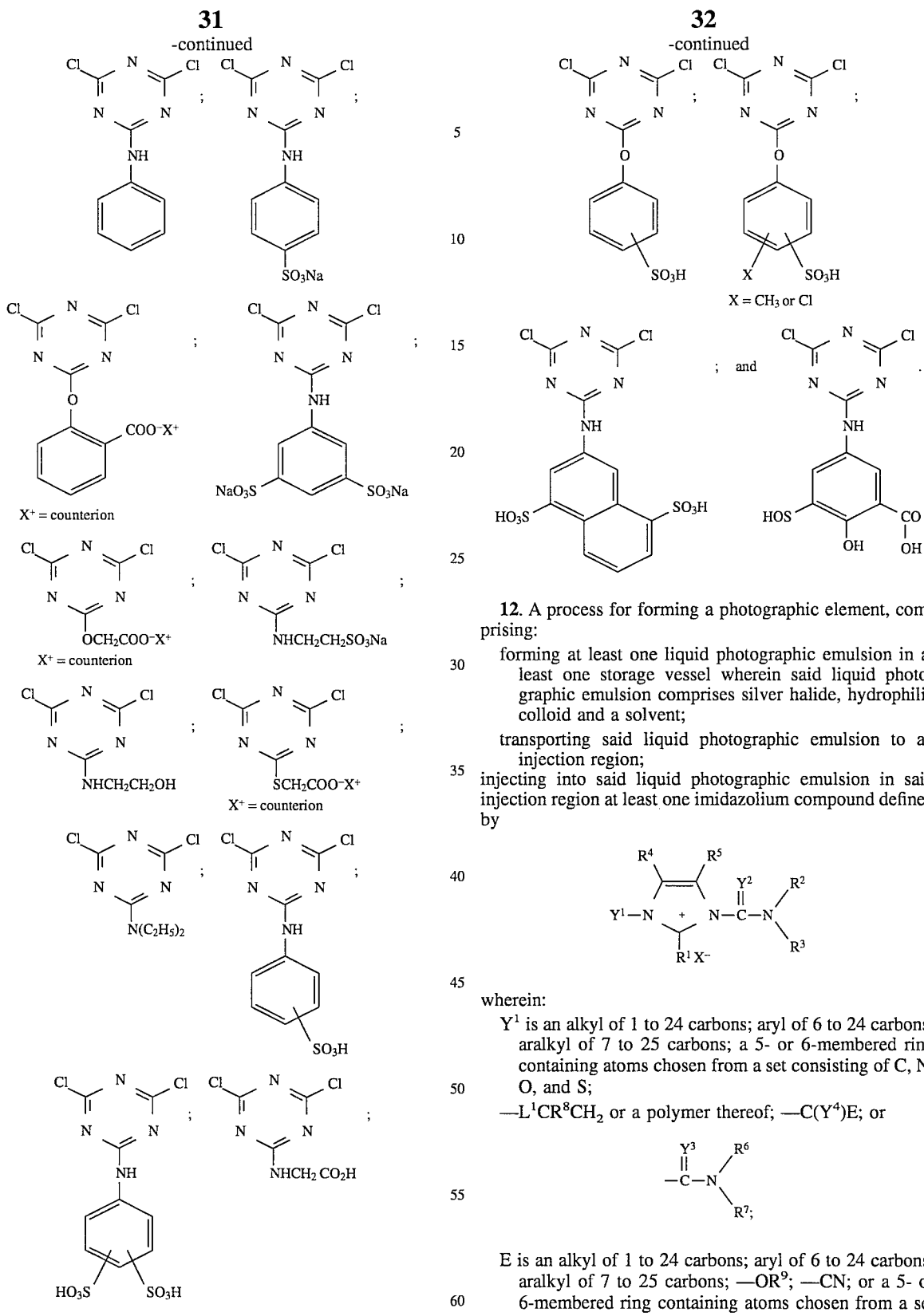

12. A process for forming a photographic element, comprising:
  forming at least one liquid photographic emulsion in at least one storage vessel wherein said liquid photographic emulsion comprises silver halide, hydrophilic colloid and a solvent;
  transporting said liquid photographic emulsion to an injection region;
  injecting into said liquid photographic emulsion in said injection region at least one imidazolium compound defined by wherein:
  $Y^1$ is an alkyl of 1 to 24 carbons; aryl of 6 to 24 carbons; aralkyl of 7 to 25 carbons; a 5- or 6-membered ring containing atoms chosen from a set consisting of C, N, O, and S;
  —$L^1CR^8CH_2$ or a polymer thereof; —$C(Y^4)E$; or E is an alkyl of 1 to 24 carbons; aryl of 6 to 24 carbons; aralkyl of 7 to 25 carbons; —$OR^9$; —CN; or a 5- or 6-membered ring containing atoms chosen from a set consisting of C, N, O, and S;

$L^1$ is a linking group;

$R^1$ is hydrogen; alkyl of 1 to 24 carbons; aryl of 6 to 24 carbons; aralkyl of 7 to 25 carbons; —$OR^{10}$; halogen; nitro; carboxyl; mercapto; alkylamino of 1 to 24 carbons; or a 5- or 6-membered ring containing atoms chosen from a set consisting of C, N, O, and S;

$R^2$ and $R^3$ independently represent hydrogen; alkyl of 1 to 24 carbons; aryl of 6 to 24 carbons; aralkyl of 7 to 25 carbons; or $R^2$ and $R^3$ independently represent, or are taken together to represent, a 5- or 6-membered ring containing atoms chosen from a set consisting of C, N, O, and S;

$R^4$ and $R^5$ independently represent hydrogen; alkyl of 1 to 24 carbons; aryl of 6 to 24 carbons; aralkyl of 7 to 25 carbons; nitro; carboxyl; mercapto; —$OR^{11}$; halogen; alkylamino of 1 to 24 carbons; or a 5- or 6-membered ring containing atoms chosen from a set consisting of C, N, O, and S; or $R^4$ and $R^5$ taken together represent a 5- or 6-membered ring containing atoms chosen from a set consisting of C, N, O, and S;

$X^-$ is a counterion;

$Y^2$, $Y^3$ and $Y^4$ independently represent O or S;

$R^6$ and $R^7$ independently represent hydrogen; alkyl of 1 to 24 carbons; aryl of 6 to 24 carbons; aralkyl of 7 to 25 carbons; or a 5- or 6-membered ring containing atoms chosen from a set consisting of C, N, O, and S; or $R^6$ and $R^7$ taken together represent a 5- or 6-membered ring containing atoms chosen from a set consisting of C, N, O, and S;

$R^8$ represents a hydrogen; an alkyl of 1 to 24 carbons; —$C(O)R^{28}$; —CN; or an aryl of 6 to 24 carbons;

$R^9$ represents hydrogen; alkyl of 1 to 24 carbons; or aryl of 6 to 24 carbons;

$R^{10}$ and $R^{11}$ independently represent hydrogen, or an alkyl of 1 to 5 carbons; and $R^{28}$ represents hydrogen; alkyl of 1 to 24 carbons; alkoxy of 1 to 24 carbons; amine; or alkylamine of 1 to 24 carbons;

transporting said liquid photographic emulsion to a coater;

coating said liquid photographic emulsion on a substrate; and removing said solvent from said liquid photographic emulsion to form a dry coated emulsion layer.

13. The process of claim 12, wherein said at least one imidazolium compound is:

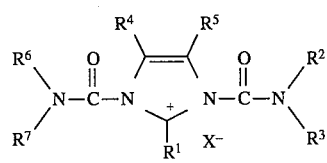

wherein:

$R^2$ and $R^3$ are each independently alkyl of 1–3 carbon atoms, a phenyl group, or a benzyl group; or $R^2$ and $R^3$ together form a five or six member having 1 or 2 nitrogen atoms and 0 or 1 oxygen atom, and one of said nitrogen atoms is unsubstituted or substituted with a methyl, ethyl, or propyl group;

$R^6$ and $R^7$ each independently represent alkyl of 1–3 carbon atoms, a phenyl group, or a benzyl group; or $R^6$ and $R^7$ taken together form a five or six member saturated ring having 1 or 2 nitrogen atoms and 0 or 1 oxygen atom, and one of said nitrogen atoms is unsubstituted or substituted with a methyl, ethyl, or propyl group;

R1, R4 and R5 independently are hydrogen or an alkyl group with 1–3 carbon atoms; and $X^-$ is an anion.

14. The process of claim 13, wherein said at least one imidazolium compound is selected from a group consisting of:

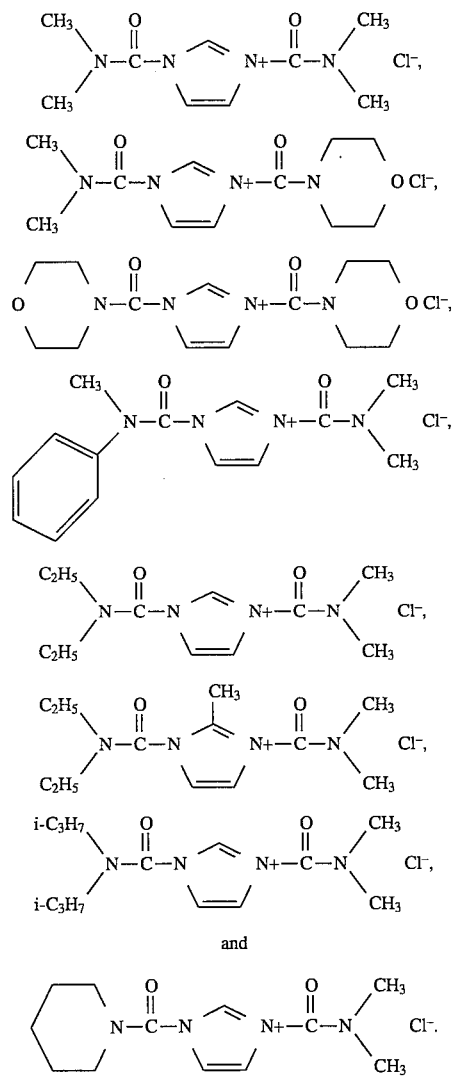

and

15. The process of claim 12, wherein in said at least one imidazolium compound:

$Y^2$ represents O;

$R^1$ is hydrogen; alkyl of 1 to 24 carbons; aryl of 6 to 24 carbons; aralkyl of 7 to 25 carbons; or halogen;

$R^2$ and $R^3$ independently represent hydrogen; alkyl of 1 to 24 carbons; aryl of 6 to 24 carbons; or aralkyl of 7 to 25 carbons; or $R^2$ and $R^3$ independently represent a 5- or 6-membered ring containing atoms chosen from a set consisting of C, N, O, and S; or $R^2$ and $R^3$ taken together represent a 5- or 6-membered ring containing atoms chosen from a set consisting of C, N, O, and S;

$Y^1$ is $$-\overset{Y^3}{\underset{\|}{C}}-N\overset{R^6}{\underset{R^7}{\diagdown}}$$

wherein $Y^3$ is O; and $R^6$ and $R^7$ independently represent hydrogen; alkyl of 1 to 24 carbons; aryl of 6 to 24 carbons; aralkyl of 7 to 25 carbons; or a 5- or 6-membered ring containing atoms chosen from a set consisting of C, N, O, and S; or $R^6$ and $R^7$ taken together represent a 5- or 6-membered ring containing atoms chosen from a set consisting of C, N, O, and S.

16. The process of claim 15, wherein said at least one imidazolium compound is chosen from a set consisting of:

[chemical structures]

17. The process for forming a photographic element of claim 12, wherein in said at least one imidazolium compound:

$Y^1$ is an alkyl of 1 to 24 carbons; aryl of 6 to 24 carbons; a 5- or 6-membered ring containing atoms chosen from a set consisting of C, N, O, and S; or $-L^1CR^8CH_2$ or a polymer thereof;

$L^1$ is a linking group; and $R^8$ represents a hydrogen; or alkyl of 1 to 3 carbons.

18. The process of claim 17, wherein said at least one imidazolium compound is chosen from a set consisting of:

[chemical structures]

19. The process of claim 12, further comprising:

forming a second hydrophilic colloid solution in a solvent;

transporting said second hydrophilic colloid solution to a second injection region;

injecting into said second hydrophilic colloid solution in said second injection region at least one triazine compound defined by

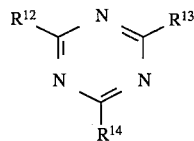

wherein:

at least two of $R^{12}$, $R^{13}$ and $R^{14}$ are independently chosen from a set consisting of halogen;

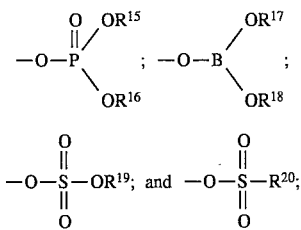

one of $R^{12}$, $R^{13}$ and $R^{14}$ represents hydrogen; alkyl of 1 to 24 carbons; halogen; —$OR^{21}$; —$NR^{22}R^{23}$; —OM; a divalent linking group to another triazine compound; sulfonamide; alkylether of 1 to 20 carbons; polyethylene oxide of 2 to 40 carbons; —$(OR^{24})_xR^{25}$; or —$L^2CR^{26}CH_2$ or a polymer thereof;

$R^{15}$ and $R^{16}$ independently represent sodium; potassium; ammonium; alkyl ammonium of 1 to 20 carbons; hydrogen; or alkyl of 1 to 20 carbons;

$R^{17}$ and $R^{18}$ independently represent sodium; potassium; ammonium; hydrogen; alkyl ammonium of 1 to 20 carbons; or alkyl of 1 to 20 carbons;

$R^{19}$ and $R^{20}$ independently represent sodium; potassium; hydrogen; ammonium; alkyl ammonium of 1 to 20 carbons; or alkyl of 1 to 20 carbons;

$R^{21}$ represents hydrogen; alkyl of 1 to 20 carbons; alkoxyalkyl of 1 to 40 carbons; aryl of 6 to 40 carbons; aralkyl of 7 to 41 carbons; or alkylthioether of 1 to 40 carbons;

$R^{22}$ and $R^{23}$ independently represent hydrogen; alkyl of 1 to 20 carbons; aryl of 6 to 20 carbons; alkylether of 1 to 20 carbons; arylether of 6 to 20 carbons; alkylthioether of 1 to 20 carbons; arylthioether of 6 to 20 carbons; sulfonyl; or alkylsulfonyl of 1 to 20 carbons;

$R^{24}$ represents an ethylene;

$R^{25}$ represents an alkyl of 1 to 20 carbons; or an ether of 1 to 20 carbons;

$R^{26}$ represents a hydrogen or alkyl of 1 to 24 carbons;

$L^2$ is a chemical linkage;

M is a counterion; and x is an integer from 1 to 24;

transporting said second hydrophilic colloid solution to said coater;

coating said second hydrophilic colloid solution on said liquid photographic emulsion or on said dry coated emulsion layer thereby forming a liquid layer; and removing said solvent from said second hydrophilic colloid solution to form a dry coated layer.

20. The process of claim 19, wherein in said at least one triazine compound:

two of $R^{12}$, $R^{13}$ and $R^{14}$ are halogen;

one of $R^{12}$, $R^{13}$ and $R^{14}$ is —$OR^{21}$; —$NR^{22}R^{23}$; —OM; a divalent linking group; sulfonamide; or amino;

$R^{21}$ represents hydrogen; alkyl of 1 to 20 carbons; alkoxyalkyl of 1 to 40 carbons; aryl of 6 to 10 carbons; aralkyl of 7 to 41 carbons; or alkyl thioether of 1 to 40 carbons;

$R^{22}$ and $R^{23}$ independently represent hydrogen; alkyl of 1 to 20 carbons; aryl of 6 to 20 carbons; alkyl ether of 1 to 20 carbons; aryl ether of 6 to 20 carbons; alkyl thioether of 1 to 20 carbons; aryl thioether of 6 to 20 carbons; sulfonyl; or alkyl sulfonyl of 1 to 20 carbons;

$R^{24}$ represents an ethylene;

$R^{25}$ represents an alkyl of 1 to 20 carbons; or an ether of 1 to 20 carbons;

$R^{26}$ represents a hydrogen; or alkyl of 1 to 24 carbons;

$L^2$ is a chemical linkage;

M is a counterion chosen from a set consisting of sodium; potassium; lithium; calcium; barium; strontium; ammonium; and alkyl ammonium with 1 to 20 carbons; and x is an integer from 1 to 24.

21. The process of claim 20, wherein said at least one triazine compound is chosen from a set consisting of:

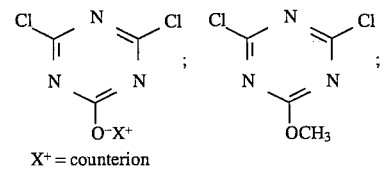

$X^+$ = counterion

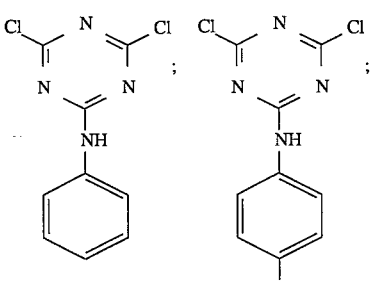

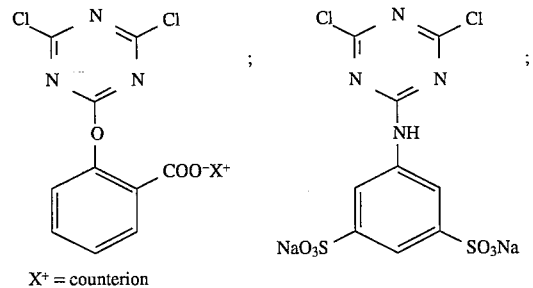

$X^+$ = counterion

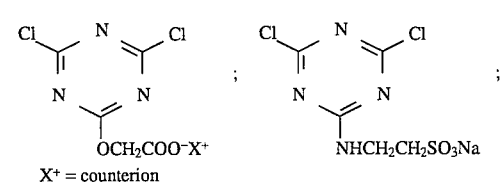

$X^+$ = counterion

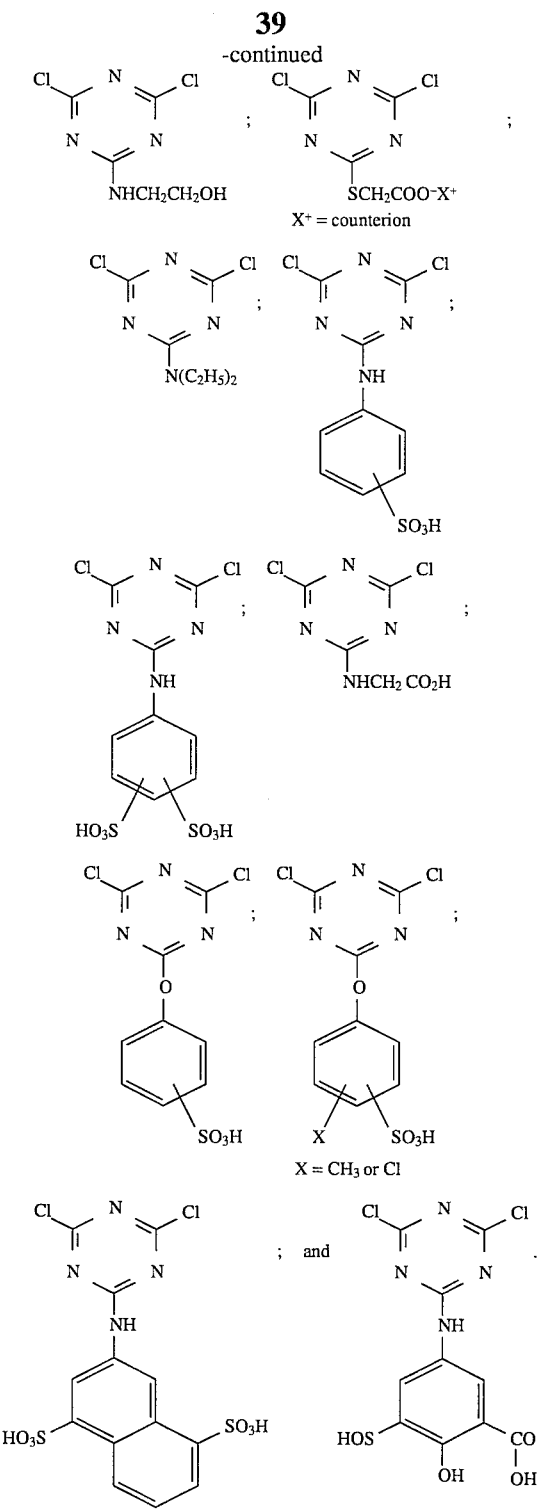

22. A photographic element comprising a silver halide containing photosensitive layer and at least one hydrophilic colloid layer hardened with at least one imidazolium compound of formula:

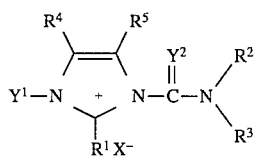

wherein:

$Y^1$ is an alkyl of 1 to 24 carbons; aryl of 6 to 24 carbons; aralkyl of 7 to 25 carbons; a 5- or 6-membered ring containing atoms chosen from the group consisting of C, N, O, and S; —$L^1CR^8CH_2$ or a polymer thereof; —$C(Y^4)E$; or

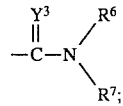

E is an alkyl of 1 to 24 carbons; aryl of 6 to 24 carbons; aralkyl of 7 to 25 carbons; —$OR^9$; —CN; or a 5- or 6-membered ring containing atoms chosen from the group consisting of C, N, O, and S;

$L^1$ is a linking group;

$R^1$ is hydrogen; alkyl of 1 to 24 carbons; aryl of 6 to 24 carbons; aralkyl of 7 to 25 carbons; —$OR^{10}$; halogen; nitro; carboxyl; mercapto; alkylamino of 1 to 24 carbons; or a 5- or 6-membered ring containing atoms chosen from the group consisting of C, N, O, and S;

$R^2$ and $R^3$ independently represent hydrogen; alkyl of 1 to 24 carbons; aryl of 6 to 24 carbons; aralkyl of 7 to 25 carbons; or a 5- or 6-membered ring containing atoms chosen from the group consisting of C, N, O, and S; or $R^2$ and $R^3$ taken together represent a 5- or 6-membered ring containing atoms chosen from the group consisting of C, N, O, and S;

$R^4$ and $R^5$ independently represent hydrogen; alkyl of 1 to 24 carbons; aryl of 6 to 24 carbons; aralkyl of 7 to 25 carbons; nitro; carboxyl; mercapto; —$OR^{11}$; halogen; alkylamino of 1 to 24 carbons; or a 5- or 6-membered ring containing atoms chosen from the group consisting of C, N, O, and S; or $R^4$ and $R^5$ taken together represent a 5- or 6-membered ring containing atoms chosen from the group consisting of C, N, O, and S;

$X^-$ is a counterion;

$Y^2$, $Y^3$ and $Y^4$ independently represent O or S;

$R^6$ and $R^7$ independently represent hydrogen; alkyl of 1 to 24 carbons; aryl of 6 to 24 carbons; aralkyl of 7 to 25 carbons; or a 5- or 6-membered ring containing atoms chosen from the group consisting of C, N, O, and S; or $R^6$ and $R^7$ taken together represent a 5- or 6-membered ring containing atoms chosen from the group consisting of C, N, O, and S;

$R^8$ represents a hydrogen; alkyl of 1 to 24 carbons; —$C(O)R^{28}$; —CN; or aryl of 6 to 24 carbons;

$R^9$ represents hydrogen; alkyl of 1 to 24 carbons; or aryl of 6 to 24 carbons;

$R^{10}$ and $R^{11}$ independently represent hydrogen or alkyl of 1 to 5 carbons; and $R^{28}$ represents hydrogen; alkyl of 1 to 24 carbons; alkoxy of 1 to 24 carbons; amine; or alkylamine of 1 to 24 carbons; and said at least one hydrophilic colloid layer, or at least another hydrophilic colloid layer, is hardened by at least one triazine compound defined by:

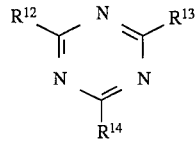

wherein:
at least two of $R^{12}$, $R^{13}$ and $R^{14}$ are independently chosen from the group consisting of halogen;

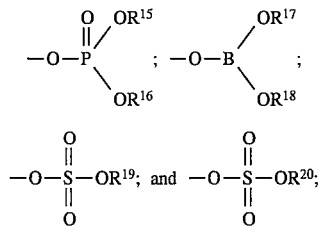

one of $R^{12}$, $R^{13}$ and $R^{14}$ represents hydrogen; alkyl of 1 to 24 carbons; halogen; —$OR^{21}$; —$NR^{22}R^{23}$; —OM; a divalent linking group to another triazine compound; sulfonamide; alkylether of 1 to 20 carbons; polyethylene oxide of 2 to 40 carbons; —$(OR^{24})_xR^{25}$; or —$L^2CR^{26}CH_2$ or a polymer thereof;

$R^{15}$ and $R^{16}$ independently represent sodium; potassium; ammonium; alkyl ammonium of 1 to 20 carbons; hydrogen; or alkyl of 1 to 20 carbons;

$R^{17}$ and $R^{18}$ independently represent sodium; potassium; ammonium; hydrogen; alkyl ammonium of 1 to 20 carbons; or alkyl of 1 to 20 carbons;

$R^{19}$ and $R^{20}$ independently represent sodium; potassium; hydrogen; ammonium; alkyl ammonium of 1 to 20 carbons; or alkyl of 1 to 20 carbons;

$R^{21}$ represents hydrogen; alkyl of 1 to 20 carbons; alkoxyalkyl of 1 to 40 carbons; aryl of 6 to 40 carbons; aralkyl of 7 to 41 carbons; or alkylthioether of 1 to 40 carbons;

$R^{22}$ and $R^{23}$ independently represent hydrogen; alkyl of 1 to 20 carbons; aryl of 6 to 20 carbons; alkylether of 1 to 20 carbons; arylether of 6 to 20 carbons; alkylthioether of 1 to 20 carbons; arylthioether of 6 to 20 carbons; sulfonyl; or alkylsulfonyl of 1 to 20 carbons;

$R^{24}$ represents an ethylene;

$R^{25}$ represents an alkyl of 1 to 20 carbons; or an ether of 1 to 20 carbons;

$R^{26}$ represents a hydrogen or alkyl of 1 to 24 carbons;

$L^2$ is a chemical linkage;

M is a counterion; and x is an integer from 1 to 24.

23. The photographic element of claim 22, wherein in said at least one imidazolium compound:

$Y^2$ represents O;

$R^1$ is hydrogen; alkyl of 1 to 24 carbons; aryl of 6 to 24 carbons; aralkyl of 7 to 25 carbons; or halogen;

$R^2$ and $R^3$ independently represent hydrogen; alkyl of 1 to 24 carbons; aryl of 6 to 24 carbons; aralkyl of 7 to 25 carbons; or $R^2$ and $R^3$ independently represent a 5- or 6-membered ring containing atoms chosen from a set consisting of C, N, O, and S; or $R^2$ and $R^3$ taken together represent a 5- or 6-membered ring containing atoms chosen from a set consisting of C, N, O, and S;

$Y^1$ is

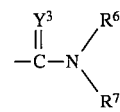

wherein $Y^3$ is O; and $R^6$ and $R^7$ independently represent hydrogen; alkyl of 1 to 24 carbons; aryl of 6 to 24 carbons; aralkyl of 7 to 25 carbons; or a 5- or 6-membered ring containing atoms chosen from a set consisting of C, N, O, and S; or $R^6$ and $R^7$ taken together represent a 5- or 6-membered ring containing atoms chosen from a set consisting of C, N, O, and S.

24. The photographic element of claim 23, wherein said at least one imidazolium compound is chosen from a set consisting of:

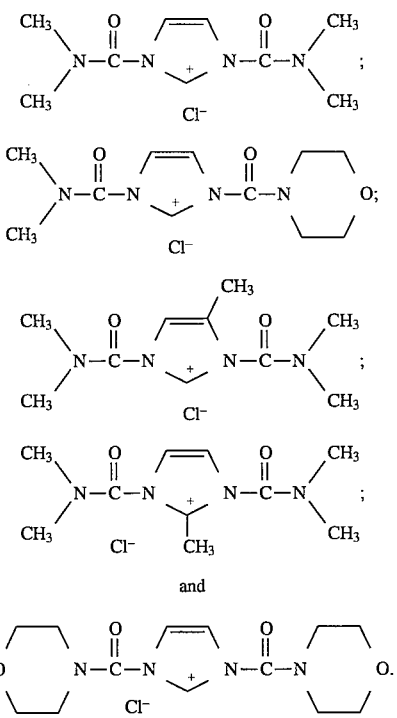

25. The photographic element of claim 22, wherein in said at least one imidazolium compound:

$Y^1$ is an alkyl of 1 to 24 carbons; aryl of 6 to 24 carbons; a 5- or 6-membered ring containing atoms chosen from a set consisting of C, N, O, and S; or —$L^1CR^8CH_2$ or a polymer thereof;

$L^1$ is a linking group; and $R^8$ represents a hydrogen; or alkyl of 1 to 3 carbons.

26. The photographic element of claim 25, wherein said at least one imidazolium compound is chosen from a set consisting of:

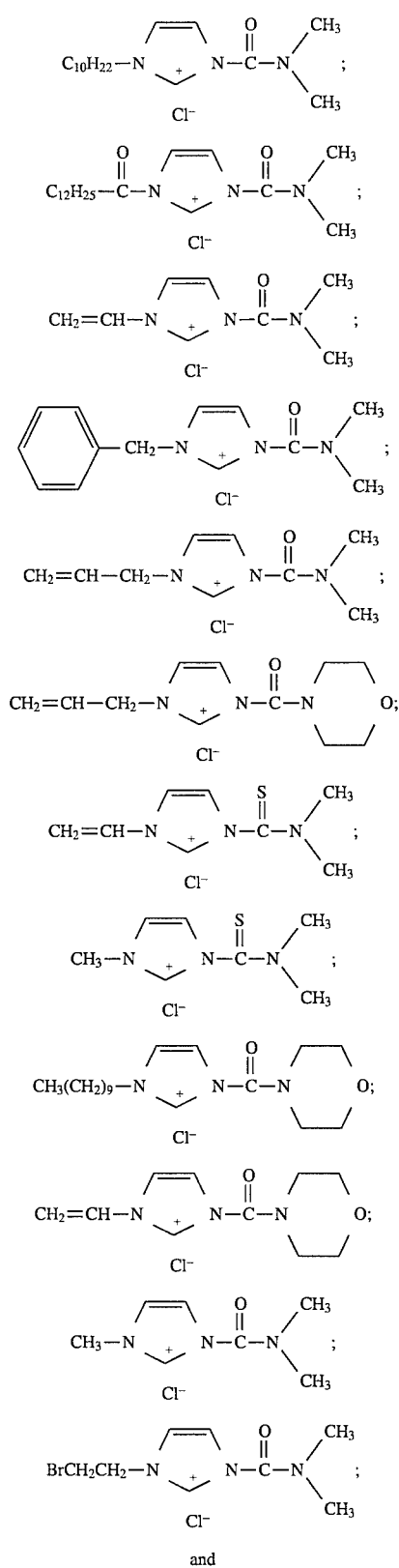

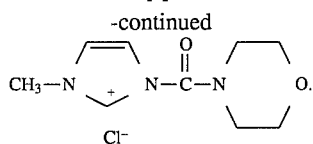

27. The photographic element of claim 22, wherein:
   at least two of $R^{12}$, $R^{13}$ and $R^{14}$ are halogen;
   one of $R^{12}$, $R^{13}$ and $R^{14}$ is —$OR^{21}$; —$NR^{22}R^{23}$; —OM; a divalent linking group; sulfonamide; or amino;
   $R^{21}$ represents hydrogen; alkyl of 1 to 20 carbons; alkoxyalkyl of 1 to 40 carbons; aryl of 6 to 10 carbons; aralkyl of 7 to 41 carbons; or alkyl thioether of 1 to 40 carbons;
   $R^{22}$ and $R^{23}$ independently represent hydrogen; alkyl of 1 to 20 carbons; aryl of 6 to 20 carbons; alkylether of 1 to 20 carbons; aryl ether of 6 to 20 carbons; alkyl thioether of 1 to 20 carbons; aryl thioether of 6 to 20 carbons; sulfonyl; or alkyl sulfonyl of 1 to 20 carbons;
   $R^{24}$ represents an ethylene;
   $R^{25}$ represents an alkyl of 1 to 20 carbons; or an ether or 1 to 20 carbons;
   $R^{26}$ represents a hydrogen or alkyl of 1 to 24 carbons;
   $L^2$ is a chemical linkage;
   M is a counterion chosen from a set consisting of sodium; potassium; lithium; calcium; barium; strontium; ammonium; or alkyl ammonium with 1 to 20 carbons; and
   x is an integer from 1 to 24.

28. The photographic element of claim 27, wherein said at least one triazine compound is chosen from a set consisting of:

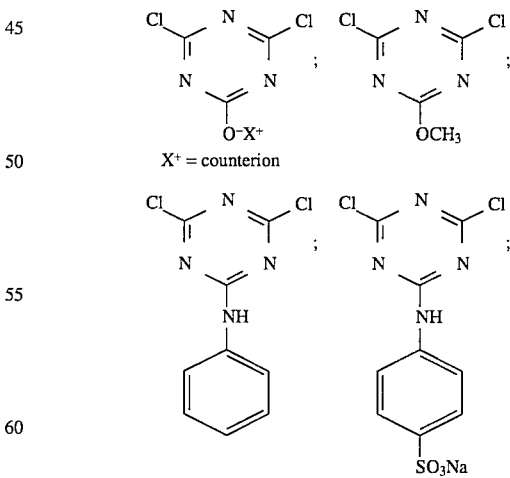

45
-continued
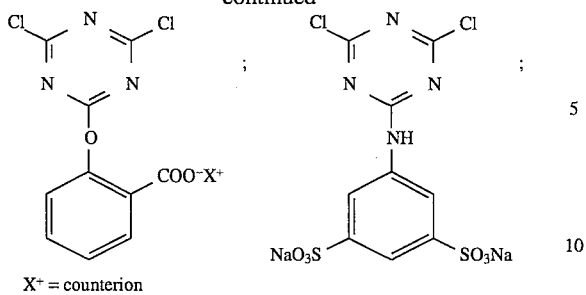
X⁺ = counterion
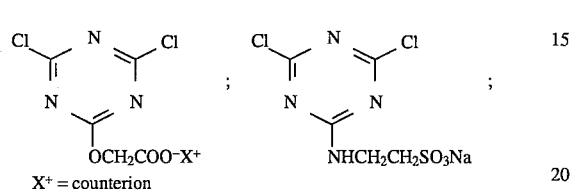
X⁺ = counterion
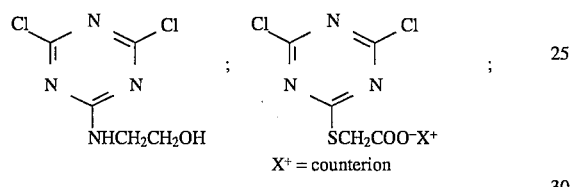
X⁺ = counterion
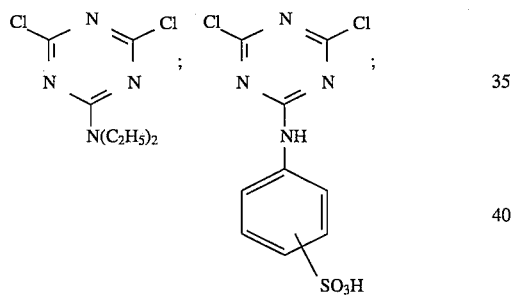
46
-continued
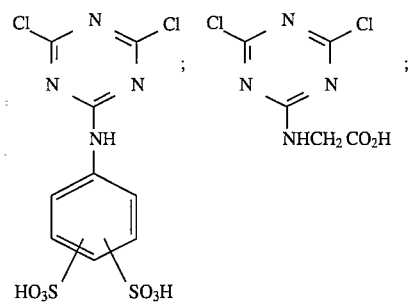
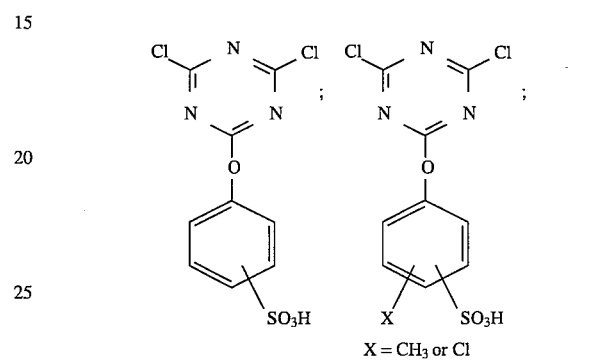
X = CH₃ or Cl
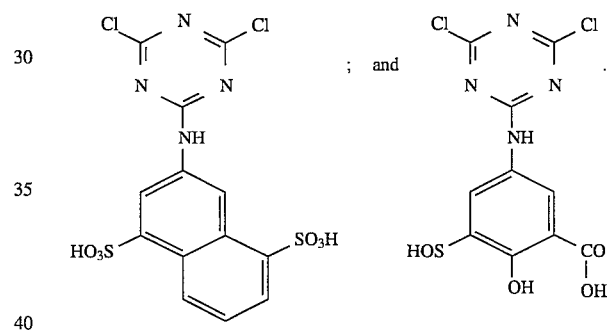
; and
* * * * *